United States Patent
Cavaletti et al.

(10) Patent No.: US 10,201,593 B2
(45) Date of Patent: Feb. 12, 2019

(54) **METHOD OF TREATING GLUTEN INTOLERANCE BY MEANS OF NEW S8/S53 ENDOPETIDASES FROM THE ACTINOMYCETE *ACTINOALLOMURUS***

(71) Applicant: Fondazione Istituto Insubrico di Ricerca Per La Vita, Gerenzano (IT)

(72) Inventors: Linda Cavaletti, Rovellasca (IT); Lucia Carrano, Legnano (IT); Monica Abbondi, Cabiate (IT); Mara Brunati, Olgiate Comasco (IT); Anna Taravella, Saronno (IT)

(73) Assignee: Fondazione Is. Insubrico di Ricerca per la Vita, Gerenzano (IT)

( * ) Notice: Subject to any disclaimer, the term of this patent is extended or adjusted under 35 U.S.C. 154(b) by 0 days.

(21) Appl. No.: 14/949,503

(22) Filed: Nov. 23, 2015

(65) Prior Publication Data

US 2016/0114009 A1  Apr. 28, 2016

Related U.S. Application Data

(62) Division of application No. 14/356,122, filed as application No. PCT/EP2012/072816 on Nov. 5, 2012, now abandoned.

(30) Foreign Application Priority Data

Dec. 6, 2011 (EP) .................................... 11425291

(51) Int. Cl.
  *A61K 38/48* (2006.01)
  *C12N 9/52* (2006.01)
  *A23J 3/34* (2006.01)
  *A23L 2/52* (2006.01)
  *A23L 33/10* (2016.01)

(52) U.S. Cl.
  CPC ............. *A61K 38/482* (2013.01); *A23J 3/346* (2013.01); *A23L 2/52* (2013.01); *A23L 33/10* (2016.08); *A61K 38/48* (2013.01); *C12N 9/52* (2013.01); *A23V 2002/00* (2013.01); *C12Y 304/21026* (2013.01)

(58) Field of Classification Search
  None
  See application file for complete search history.

(56) References Cited

FOREIGN PATENT DOCUMENTS

| | | |
|---|---|---|
| WO | 2003068170 A2 | 8/2003 |
| WO | 2005107786 A1 | 11/2005 |
| WO | 2011077359 A2 | 6/2011 |

OTHER PUBLICATIONS

Tuckova et al, Activation of macrophages by food antigens: enhancing effect of gluten on nitric oxide and cytokine production. Journal of Leukocyte Biology vol. 67, Mar. 2000 p. 312-318.*
Shan et al, Structural Basis for Gluten Intolerance in Celiac Sprue. Science vol. 29727 Sep. 2002 p. 2275-79.*
Prandi et al, Composition of peptide mixtures derived from simulated gastrointestinal digestion of prolamins from different wheat varieties. Journal of Cereal Science 56 (2012) 223-231.*
Comino et al, Monitoring of gluten-free diet compliance in celiac patients by assessment of gliadin 33-mer equivalent epitopes in feces. Am J Clin Nutr 2012;95:670-7.*
Sollid et al, Nomenclature and listing of celiac disease relevant gluten T-cell epitopes restricted by HLA-DQ molecules. Immunogenetics (2012) 64:455-460.*
"PeptideCutter" trypsin cleavage of SEQ ID No. 2. Performed Jan. 26, 2018.*
"PeptideCutter" chymotrypsin cleavage of SEQ ID No. 2. Performed Jan. 26, 2018.*
Pozzi, et al., "The genus *Actinoallomurus* and some of its metabolites," The Journal of Antibiotics (2011) 64, 133-139, published on line Dec. 1, 2010.
Search Report of PCT/EP2012/071816 dated Feb. 26, 2013.
Written Opinion of PCT/EP2012/071816 dated Feb. 26, 2013.
Dressman J.B., et al., "Upper gastrointestinal (GI) pH in young, healthy men and women," Pharmaceutical Research, vol. 7, No. 7, 1990 756-761.
Gass J., et al., "Effect of barley endoprotease EP-B2 on gluten digestion in the intact rat", JPET 318:1178-1186, 2006.
Gordon S., et al., "Computational Design of an alfa-gliadin peptidase," J. Am. Chem. Soc. 2012, 134, 20513-20520.
Mamone G., et al., "Qualitative and qualitative analysis of wheat gluten proteins by liquid chromatography and electrospray mass spectrometry," Rapid Commun. Mass Spectrom. 14, 897-904 (2000).

* cited by examiner

*Primary Examiner* — Sheridan Swope
(74) *Attorney, Agent, or Firm* — Silvia Salvadori, P.C.; Silvia Salvadori

(57) ABSTRACT

The invention relates to a new family of proteolytic enxymes having the ability to hydrolize at a pH between 3 and 8 gluten olygopeptides which are resistant to cleavage by gastric and pancreatic enzymes and whose presence in the intestinal lumen results in toxic effects. The enzymes have been identified as endopeptidases of the S8/S53 family and are produced by an *Actinoallomurus* strain.

The object of the invention includes also methods for producing enzymes composition comprising the endopeptidases by cultivation of native *Actinoallomurus* strains, mutants thereof, or recombinant host cells comprising nucleic acids codifying for the endopeptidases. Said nucleic acids constitute a further object of the invention.

The enzyme compositions comprising at least one endopeptidase of the invention are useful for the treatment and/or prevention of celiac sprue, dermatitis herpetiformis and any other disorder associated with gluten intolerance as ingredients of pharmaceutical formulations or as additives of foods and drinks.

12 Claims, 11 Drawing Sheets
Specification includes a Sequence Listing.

Breakdown of the 33-mer gliadin peptide by endopep-140 SEQ ID NO:1

Breakdown of the 33-mer gliadin peptide by endopep-140 SEQ ID NO:1 in the presence of pepsin Breakdown of the 33-mer gliadin peptide by endopep-140 SEQ ID NO:1 in the presence of pepsin lane 1 = Molecular weight marker; lane 2 = gliadin; lane 3 = gliadin + endopep-40 (<100 kDa) SEQ ID NO:2; lane 4 = gliadin + endopep-40 (<100 kDa) SEQ ID NO:2 + pepsin; lane 5 = reaction 3 stopped after 10 min incubation; lane 6 = gliadin + endopep-140 (>100 kDa) SEQ ID NO:1; lane 7 = gliadin + endopep-140 (>100 kDa) SEQ ID NO:1 + pepsin.

SEQUENCE LISTING

<160> NUMBER OF SEQ ID NOS: 15

<210> SEQ ID NO 1
<211> LENGTH: 1390
<212> TYPE: PRT
<213> ORGANISM: Actinoallomurus
<220> FEATURE:
<221> NAME/KEY: PROPEP
<222> LOCATION: (1)..(1390)

<400> SEQUENCE: 1

Met Pro Asp Leu Pro Thr Gln Arg Arg Ser Pro Arg Arg Ser Arg Arg
1               5                   10                  15

Pro Ala Val Leu Ala Arg Leu Ala Gly Leu Arg Val Gly Ala Leu Val
                20                  25                  30

Leu Ala Leu Ala Val Thr Thr Leu Thr Leu Ile Ser Met Pro Ser Ala
            35                  40                  45

Asn Ala Ala Pro Ala Lys Pro Val Val Pro His Ala Lys Ala Ser Ser
        50                  55                  60

Pro Thr Ala Gln Gly Gln His Pro Thr Ser Arg Val Cys Arg Thr Pro
65                  70                  75                  80

Gly Arg Ala Asn Glu Met Thr Cys Leu Ala Met Val Arg Asp Val
                85                  90                  95

Ile Gly Pro Lys Gly Val Gln Ala Asn Asp Ala Pro Ala Gly Phe Gly
                100                 105                 110

Pro Ala Asp Leu Leu Asn Ala Tyr Asn Leu Pro Ser Ala Gly Ser Thr
            115                 120                 125

```
Glu Thr Val Ala Ile Val Asp Ala Phe Asp Asn Pro Asn Ala Glu Ala
    130                 135                 140

Asp Leu Gly Val Tyr Arg Gln Gln Tyr Gly Leu Pro Ala Cys Thr Thr
145                 150                 155                 160

Ala Asn Gly Cys Phe Lys Lys Ile Asp Gln Arg Gly Gly Thr Ser Tyr
                165                 170                 175

Pro Pro Pro Asp Ala Gly Trp Ala Gly Glu Ile Ala Leu Asp Ile Asp
            180                 185                 190

Met Val Ser Ala Ile Cys Pro Thr Cys Lys Ile Leu Leu Val Glu Ala
        195                 200                 205

Asp Asp Asn Tyr Met Asp Asn Leu Gly Thr Ala Val Asn Gln Ala Val
    210                 215                 220

Ser Gln Gly Ala Lys Phe Val Ser Asn Ser Tyr Gly Gly Ser Glu Gly
225                 230                 235                 240

Ser Asp Glu Gly Gln Ala Asp Ala Tyr Phe His His Asp Gly Val
            245                 250                 255

Ala Ile Thr Ala Ser Ser Gly Asp Ser Gly Tyr Gly Ala Ser Tyr Pro
                260                 265                 270

Ala Ala Ser Pro Tyr Val Thr Ser Val Gly Gly Thr Ser Leu Ala Lys
                275                 280                 285

Asp Thr Ser Ser Ser Arg Gly Trp Thr Glu Ser Thr Trp Asn Gly Ala
    290                 295                 300

Gly Ser Gly Cys Ser Ala Tyr Glu Thr Lys Pro Ser Phe Gln Lys Asp
305                 310                 315                 320

Thr Gly Cys Ala Arg Arg Thr Ile Ala Asp Val Ser Ala Val Ala Asp
                325                 330                 335

Pro Asn Thr Gly Val Ala Val Tyr Asn Gly Gly Trp His Val Tyr Gly
            340                 345                 350

Gly Thr Ser Val Ser Ala Pro Ile Ile Ala Ser Val Tyr Ala Leu Gly
        355                 360                 365

Gly Ala Pro Ala Ala Gly Ser Ala Pro Asn Ser Phe Pro Tyr Asp His
    370                 375                 380

Pro Ala Asp Leu Asn Asp Val Thr Ser Gly Ser Asn Gly Ser Cys Ser
385                 390                 395                 400

Pro Ala Tyr Leu Cys Thr Ala Gly Thr Gly Tyr Asp Gly Pro Thr Gly
                405                 410                 415

Leu Gly Thr Pro Asn Gly Ile Ala Ala Phe Arg Ser Gly Pro His Ala
            420                 425                 430

Val Val Thr Gly Thr Val Thr Asp Gly Thr Ala Pro Leu Ala Ser Ala
        435                 440                 445

Gln Val Lys Ala Gly Asp Val Thr Ala Thr Asp Gly Gln Gly His
    450                 455                 460

Tyr Thr Leu Ser Val Pro Pro Gly Thr Tyr Asp Val Ser Ala Ser Lys
465                 470                 475                 480

Phe Gly Tyr Thr Gly Lys Thr Ile Ser Gly Val Gln Val Ala Asp Gly
                485                 490                 495

Gln Thr Val Thr Glu Asp Phe Ala Leu Thr Ala Lys Ala Arg Val Asp
            500                 505                 510

Val Ser Gly Leu Val Arg Asp Gly Ser Gly His Gly Trp Pro Val Tyr
        515                 520                 525

Ala Thr Val Arg Val Lys Asp Gln Pro Thr Ala Val Ala Tyr Thr Asp
    530                 535                 540
```

-continued

```
Pro Lys Thr Gly Arg Tyr Thr Leu Ser Leu Pro Thr Asp Asp Thr Tyr
545                 550                 555                 560

Thr Leu Gln Val Asp Pro Leu Tyr Pro Gly Tyr Thr Gln Asp Ser His
            565                 570                 575

Asp Val Thr Val Thr Ser Ala Asp Val Val His Asp Val Asn Val Ala
                580                 585                 590

Val Asp Gln Thr Thr Cys Ser Ala Pro Gly Tyr Ser Tyr His Tyr Ala
            595                 600                 605

Gly Ala Thr Gln Pro Phe Asp Gly Thr Thr Ala Pro Ala Gly Trp Thr
            610                 615                 620

Val Asp Asp Lys Val Gly Asn Gly Gln Thr Trp Val Phe Asn Asp Pro
625                 630                 635                 640

Gly Ser Arg Gly Asn Lys Thr Gly Gly Thr Gly Gly Phe Ala Val Ile
                645                 650                 655

Asp Ser Asp His Tyr Gly Ser Gly Asn Thr Gln Asp Ser Thr Leu Phe
                660                 665                 670

Ser Pro Val Thr Asp Phe Ser Ala Arg Thr His Pro Ile Leu Ser Phe
            675                 680                 685

Arg Ser Asp Trp Tyr Gly Tyr Thr Gly Gln Ala Gly Asp Leu Asp Leu
            690                 695                 700

Ser Val Asp Gly Gly Thr Thr Trp Thr Asn Leu Lys His Tyr Thr Ala
705                 710                 715                 720

Ser Glu Arg Gly Pro Arg Thr Glu Thr Met Asp Leu Ser Ala Ala Ala
                725                 730                 735

Gly Lys Ser Ala Val Gln Val Arg Phe His Phe Thr Gly Lys Phe Gly
            740                 745                 750

Tyr Tyr Trp Gln Val Asp Asp Val Phe Leu Gly Asp Arg Thr Cys Asp
            755                 760                 765

Pro Thr Ser Gly Gly Leu Val Val Gly Gln Val Thr Asp Ala Asn Thr
770                 775                 780

Gly Ala Gly Val Ala Gly Ala Thr Val Thr Ser Val Asp Arg Pro Ala
785                 790                 795                 800

Glu His Ala Thr Ser Ala Ala Thr Pro Asp Asp Pro Asn Leu Gly Asp
            805                 810                 815

Gly Leu Phe Trp Met Phe Ser Ser Val Thr Gly Ser His Lys Phe Thr
            820                 825                 830

Ala Thr Ala Gly Asn Tyr Asp Ser His Asp Val Thr Asn Val Ala
            835                 840                 845

Ala Asn Trp Ala Thr Ala Ala Asp Ile Ala Leu Ser Ala Pro Arg Leu
850                 855                 860

Thr Val Thr Pro Gly Ala Ile Ser Lys Thr Val Gly Trp Gln Lys Ala
865                 870                 875                 880

Ala Thr Ala Ala Leu Thr Leu Lys Asn Thr Gly Thr Ser Pro Val Thr
            885                 890                 895

Ala Lys Ile Gly Glu Gln Pro Gly Gly Ser Thr Thr Ala Thr Ala Gly
                900                 905                 910

Ala Pro Leu Gln Arg Val Lys Gly Asp Phe Ala Ser Gly Arg Leu Gln
            915                 920                 925

Gln Gly Lys Ala Ser Gly Ala Lys Ala Gly Val Thr Pro Tyr Ala Pro
            930                 935                 940

Pro Trp Thr Ala Ile Ala Asp Tyr Ala Ser Pro Ile Met Asp Asn Gly
945                 950                 955                 960

Ala Val Ala Leu Asn Gly Lys Ile Tyr Ser Val Ala Gly Val Asp Gly
```

-continued

```
                965                 970                 975
Ala Asn Val Leu Asn Lys Ala Tyr Ala Tyr Asp Pro Gly Thr Gln Ala
                    980                 985                 990
Trp Thr Ala Ile Ala Pro Leu Ala  Thr Gly Arg Glu Ala  Pro Gln Ala
        995                 1000                1005
Thr Thr Thr Gly Gly Lys Leu  Tyr Val Thr Gly Gly  Trp Gly Ser
        1010                1015                1020
Thr Gly Ala Ala Val Ala Lys  Thr Glu Ile Phe Asp  Pro Ser Ser
        1025                1030                1035
Gly Ala Trp Ser Ala Gly Ala  Asp Asn Pro Lys Pro  Tyr Ala Gly
        1040                1045                1050
Ser Gly Ala Ala Val Leu Asp  Gly Lys Ile Tyr Val  Val Gly Gly
        1055                1060                1065
Cys Leu Ala Thr Cys Gly Thr  Lys Asp Val Gln Val  Tyr Asp Pro
        1070                1075                1080
Ala Ala Asn Ser Trp Ser Ser  Gly Pro Ala Tyr Pro  Glu Asn Thr
        1085                1090                1095
Ala Trp Leu Gly Cys Ala Gly  Ile Asp Gly Lys Leu  Tyr Cys Ala
        1100                1105                1110
Gly Gly Ser Ala Ala Ala Ser  Thr Lys His Gly Tyr  Val Leu Asp
        1115                1120                1125
Pro Ala Ser Gly Thr Trp Ser  Pro Ile Ala Asp Leu  Pro Ile Asp
        1130                1135                1140
Leu Trp Ala Met Gly Tyr Ser  Ala Ala Asn Gly Lys  Leu Ile Val
        1145                1150                1155
Ser Gly Gly Val Thr Asn Gly  Ala Ser Thr Leu Thr  Asn Gln Gly
        1160                1165                1170
Phe Ala Tyr Asp Pro Ser Ala  Asn Ser Trp Thr Ala  Leu Pro Asn
        1175                1180                1185
Ser Asn Asn Ala Leu Tyr Arg  Gly Ala Ser Ala Cys  Gly Phe Tyr
        1190                1195                1200
Lys Ile Gly Gly Ser Leu Gly  Gln Phe Asn Ala Val  Lys Ser Gly
        1205                1210                1215
Glu Val Leu Pro Gly Tyr Asp  Gln Cys Ala Ser Thr  Ala Asp Val
        1220                1225                1230
Pro Trp Leu Ser Glu Asp Lys  Thr Glu Val Thr Ile  Gln Pro Gly
        1235                1240                1245
Gln Ser Val Lys Val Asn Val  Thr Leu Asp Ala Asn  Val Pro Ala
        1250                1255                1260
Ile Thr Gln Pro Gly Thr Tyr  Thr Ala Gln Leu Thr  Val Gly Ala
        1265                1270                1275
Lys Thr Pro Tyr Ala Ile Pro  Pro Val Ala Val Thr  Met Thr Val
        1280                1285                1290
Asn Pro Pro Gly Thr Trp Gly  Lys Ile Thr Gly Thr  Leu Thr Gly
        1295                1300                1305
Ala Gly Cys Thr Gly Ser Pro  Ala Pro Leu Thr Gly  Ala Thr Leu
        1310                1315                1320
Gln Ile Asp Ser Trp Ala Ala  Ser Tyr Thr Leu Lys  Thr Asp Lys
        1325                1330                1335
Asn Gly Gln Tyr Ala Leu Trp  Leu Asp Val Arg Asn  Asn Pro Leu
        1340                1345                1350
Thr Leu Ile Ala Ala Lys Asp  Gly Trp Ala Pro Gln  Thr Arg Asn
        1355                1360                1365
```

```
Val Lys Ile Thr Lys Leu Thr Ser Thr Thr Ala Asp Phe Thr Leu
    1370            1375                1380

Lys Pro Asp His Thr Cys Ser
    1385            1390

<210> SEQ ID NO 2
<211> LENGTH: 398
<212> TYPE: PRT
<213> ORGANISM: Actinoallomurus sp.
<220> FEATURE:
<221> NAME/KEY: PROPEP
<222> LOCATION: (1)..(398)

<400> SEQUENCE: 2

Met Ser Arg Arg Val Thr Gly Thr Ile Leu Gly Gly Leu Ile Leu Ala
1               5                   10                  15

Met Val Pro Phe Leu Ser Thr Ala Ala Asn Ala Ala Pro Gln Ala Ala
                20                  25                  30

Pro Ala Ser Val Ser His Pro Phe His His Ser Cys Ala Thr Val Lys
            35                  40                  45

Pro Gly Arg Ala Ser Cys Asn Ala Leu Val Arg Ser Asp Ile Ala Gln
    50                  55                  60

Ser Ala Ala Thr Leu Ala His Gln Ala Ala Pro Ser Gly Leu Ser
65                  70                  75                  80

Pro Ala Asn Leu Gln Ser Ala Tyr Lys Leu Pro Ser Ser Thr Ala Gly
                85                  90                  95

Ser Gly Gln Thr Val Ala Ile Val Asp Ala Tyr Asp Ala Pro Thr Ala
            100                 105                 110

Glu Ala Asp Leu Asn Val Tyr Arg Ser Gln Phe Gly Leu Gly Ala Cys
        115                 120                 125

Thr Thr Ala Asn Gly Cys Phe Lys Lys Val Asp Gln Asn Gly Gly Thr
130                 135                 140

Ser Tyr Pro Arg Lys Asp Gly Gly Trp Ala Gln Glu Ile Ser Leu Asp
145                 150                 155                 160

Leu Asp Met Val Ser Ala Val Cys Pro Asn Cys Lys Ile Val Leu Val
                165                 170                 175

Glu Ala Lys Thr Asn Ser Phe Ala Asn Leu Gly Thr Ala Glu Asn Thr
            180                 185                 190

Ala Ala Ser Leu Ala Asn Val Ile Ser Asn Ser Tyr Gly Gly Ser Asp
        195                 200                 205

Ala Ser Asp Ala Ser Tyr Gly Ser Tyr Asn His Pro Gly Lys Ala
    210                 215                 220

Ile Thr Val Ser Ser Gly Asp Ala Gly Tyr Gly Val Glu Tyr Pro Ala
225                 230                 235                 240

Ser Ser His Tyr Val Thr Ala Val Gly Gly Thr Ser Leu Arg Thr Ala
                245                 250                 255

Ser Thr Ser Arg Gly Trp Ser Glu Thr Ala Trp Ser Gly Ala Gly Ser
            260                 265                 270

Gly Cys Ser Ala Tyr Asn Thr Ala Leu Ser Gly Gln Ser Gly Leu Thr
        275                 280                 285

Gly Cys Ser Arg Arg Ala Val Ala Asp Val Ser Ala Val Ala Asp Pro
    290                 295                 300

Ala Thr Gly Val Ala Val Tyr Asp Ser Thr Ala Tyr Gln Gly Gln Ser
305                 310                 315                 320

Gly Trp Met Val Phe Gly Gly Thr Ser Val Ala Ala Pro Ile Ile Gly
```

```
                       325                 330                 335
Gly Val Tyr Gly Leu Ala Ala Asn Ala Ala Ser Ile Asp Asn Asn Tyr
            340                 345                 350

Pro Tyr Ala His Thr Ser Ser Leu Phe Asp Val Thr Ser Gly Ser Asn
            355                 360                 365

Gly Thr Cys Thr Thr Thr Lys Trp Cys Thr Ala Gly Thr Gly Trp Asp
            370                 375                 380

Gly Pro Thr Gly Leu Gly Thr Pro Asn Gly Thr Gly Ala Phe
385                 390                 395
```

<210> SEQ ID NO 3
<211> LENGTH: 1094
<212> TYPE: PRT
<213> ORGANISM: Actinoallomurus
<220> FEATURE:
<221> NAME/KEY: PROPEP
<222> LOCATION: (1)..(1094)

<400> SEQUENCE: 3

```
Met Ser Ala Ala Val Val Ile Phe Ala Gly Ala Pro Ala Thr Ala Ala
1               5                   10                  15

Pro Thr Pro Glu Gly Ser Gly Arg His Trp Thr Ala Thr Pro Leu Ser
            20                  25                  30

Gly Thr Val Val Gln Gly Phe Lys Ser Thr Thr Gly Arg Leu Ala Lys
            35                  40                  45

Ser Asp Ala Gly Leu Leu Arg Leu Lys Ser Ser Lys Pro Val His Val
    50                  55                  60

Met Val Lys Leu Asp Tyr Asp Ser Leu Ala Ala Tyr Arg Gly Gly Ile
65                  70                  75                  80

Pro Gly Tyr Ala Ala Thr Ser Pro Ala Val Thr Gly His Thr Leu Asp
                85                  90                  95

Pro Ala Ser Ala Gly Ala Arg Arg Tyr Gln Gly Tyr Ile Gly Gly Val
            100                 105                 110

Glu Asn Arg Phe Arg Ala Ala Leu Gly Lys Arg Leu Pro Gly Ala Lys
            115                 120                 125

Ala Gly Gly Gly Leu Arg Thr Val Tyr Gly Gly Leu Ala Val Thr Leu
        130                 135                 140

Pro Gly Asp Lys Val Ala Asp Leu Leu Lys Leu Pro Gly Val Ala Ala
145                 150                 155                 160

Val Gln Glu Asp Ala Val Ala Lys Pro Leu Thr Asp Ser Ser Pro Gly
                165                 170                 175

Phe Ile Gly Ala Pro Thr Ile Tyr Lys Gln Leu Gly Gly Ser Asp Ser
            180                 185                 190

Ser Gly Lys Gly Val Ile Val Gly Asp Leu Asp Ser Gly Ala Trp Pro
        195                 200                 205

Glu His Pro Ser Tyr Lys Asp Ser Gly Lys Leu Pro Ala Pro Pro
    210                 215                 220

Thr Thr Asp Gly Ala Pro Arg Pro Cys Asp Phe Gly Asp Asn Pro Leu
225                 230                 235                 240

Thr Pro Ala Asn Asp Pro Tyr Val Cys Asp His Lys Leu Ile Ser Gly
                245                 250                 255

Gln Pro Phe Leu Asp Thr Tyr Asn Ala Val Val Gly Gly Glu Arg Phe
            260                 265                 270

Pro Asp Ser Ala Arg Asp Ser Asp Gly His Gly Thr His Thr Ser Thr
        275                 280                 285
```

```
Thr Ala Ala Gly Ser Ala Val Ser His Ala Asn Pro Leu Gly Ile Asp
    290                 295                 300
Arg Gly Ala Ile His Gly Ile Ala Pro Ala Ala His Ile Ala Val Tyr
305                 310                 315                 320
Lys Val Cys Gly Ala Gln Gly Cys Phe Gln Ser Asp Ser Val Ala Ala
                325                 330                 335
Val Gln Arg Ala Ile Leu Asp Lys Val Arg Val Ile Asn Tyr Ser Ile
            340                 345                 350
Ser Gly Gly Val Asp Pro Tyr Ser Asp Pro Val Glu Leu Ala Phe Leu
        355                 360                 365
Asp Ala Tyr Ala Ala Gly Val Leu Val Ser Ala Ser Ala Gly Asn Asp
370                 375                 380
Gly Pro Thr Ala Gly Thr Val Asn His Asn Gly Pro Trp Val Thr Thr
385                 390                 395                 400
Val Ala Ala Ser Thr Gln Gln Arg Thr Phe Gln Ser Thr Val Thr Leu
                405                 410                 415
Gln Ala Gly Gly Ala Ser Leu Lys Leu Ala Gly Ser Ser Ile Thr Ser
            420                 425                 430
Gly Ile Thr Ser Pro Leu Pro Val Val Leu Ala Ser Ala Ala Pro Tyr
        435                 440                 445
Gly Asp Pro Asp Cys Asp Thr Gln Ala Ala Pro Gly Thr Phe Thr Gly
450                 455                 460
Lys Ile Val Ala Cys Arg Leu Leu Asn Arg Gly Arg Ile Met Lys Gly
465                 470                 475                 480
Tyr Asn Val Phe Lys Gly Gly Ala Ala Gly Met Leu Leu Tyr Asn Asp
                485                 490                 495
Thr Leu Ser Gln Thr Met Thr Asp Asn His Trp Leu Pro Thr Val His
            500                 505                 510
Leu Glu Lys Pro Gln Ala Asp Ala Leu Leu Ala Phe Leu Ser Gly His
        515                 520                 525
Thr Gly Thr Thr Ala Thr Phe Pro Gln Gly Ala Lys Ala Asn Gly Gln
530                 535                 540
Gly Asp Val Met Thr Ala Phe Ser Ser Arg Gly Pro Gly Gly Asp Phe
545                 550                 555                 560
Leu Lys Pro Asp Val Thr Ala Pro Gly Leu Gln Ile Met Gly Gly Gln
                565                 570                 575
Thr Pro Val Pro Asp Asp Pro Ser Leu Gly Pro Pro Gly Thr Leu Tyr
            580                 585                 590
Gln Val Ile Ala Gly Thr Ser Met Ser Ala Pro His Val Thr Gly Ala
        595                 600                 605
Ala Ala Leu Leu Phe Ala Leu His Pro Ser Trp Thr Pro Gly Gln Val
610                 615                 620
Lys Ser Ala Leu Glu Thr Thr Gly Lys Thr Ser Val Val Lys His Asp
625                 630                 635                 640
Arg Lys Thr Pro Ala Asp Pro Phe Asp Leu Gly Gly Gly Arg Ile Asp
                645                 650                 655
Leu Thr Lys Ala Gly Asp Pro Gly Leu Thr Ile Asp Glu Thr Ala Ala
            660                 665                 670
Asn Tyr Ala Ala Ser Ala Thr Asp Pro Leu His Arg Ile Asp Leu Asn
        675                 680                 685
Val Pro Ser Val Asn Ala Pro Val Met Pro Gly Ala Ile Met Thr Thr
690                 695                 700
Arg Thr Val Lys Asn Val Ser Gly Lys Thr Met Thr Tyr Gly Thr Ser
```

```
            705                 710                 715                 720
Gly Thr Thr Val Lys Gly Ala Ser Ile Ser Val Ser Pro Gly Thr Phe
                        725                 730                 735
Thr Val Lys Pro Gly Lys Thr Ala Arg Leu Arg Ile Thr Ile Ala Ala
                    740                 745                 750
Pro Ala Leu Ala Asn Gly Gln Tyr Phe Gly Arg Val Asp Leu Arg Gln
                755                 760                 765
Arg Asn Gly Gly His Asp Leu His Leu Pro Val Ala Phe Val Arg Lys
770                 775                 780
Gln Gly Val Val Ser Leu Asn Gln Thr Cys Thr Pro Ser Val Ile Ala
785                 790                 795                 800
Leu Asn Ser Gly Arg Ser Thr Cys Asp Val Asp Val Glu Asn Thr Ser
                    805                 810                 815
Leu Ala Asp Thr Lys Val Ile Ala Ala Ser His Leu Asp Thr Arg Leu
                820                 825                 830
Arg Leu Thr Ala Val Thr Gly Ala Thr Lys Val Gly Ala His Asp Val
                835                 840                 845
Leu Ala Gln Ala Asp Leu Ala Arg Arg Gln Pro Asp Lys Pro Gln Ile
850                 855                 860
Ala Pro Gly Ala Thr Pro Ala Gly Tyr Leu Pro Leu Asp Ala Phe Gly
865                 870                 875                 880
Ile Pro Pro Thr Pro Ile Gly Asp Glu Gln Ser Leu Asn Leu Thr Thr
                    885                 890                 895
Pro Ala Phe Thr Phe Ala Gly Arg Thr Tyr Thr Ser Leu Gly Val Val
                900                 905                 910
Ser Asp Gly Tyr Thr Val Ala Gly Gly Ala Thr Pro Asp Asp Val Ala
                915                 920                 925
Ala Thr Pro Gln Thr Leu Pro Asn Pro Ala Arg Pro Asn Gly Glu Leu
                930                 935                 940
Ala Pro Phe Trp Thr Asp Leu Asp Gly Ala Gly Ala Pro Gly Val Tyr
945                 950                 955                 960
Ala Ala Arg Leu Thr Asp Gly Thr Ser Thr Trp Ile Val Val Glu Trp
                965                 970                 975
Arg Leu Asn Val Phe Gly Thr Asn Ser Leu Arg Val Phe Gln Gln Trp
                980                 985                 990
Ile Gly Val Asn Gly Ala Glu Asp Ile Ser Tyr Thr Tyr Asp Pro Asn
                995                 1000                1005
Asn Leu Pro Ala Ala Pro Ala Gly Tyr Gly Leu Thr Val Gly
    1010                1015                1020
Ala Glu Asn Asp Glu Gly Thr Ala Gly Ser Gln Ile Ser Gly Thr
    1025                1030                1035
Pro Thr Glu Asp Leu Arg Val Thr Ser Thr Pro Gly Ala Ala Gly
    1040                1045                1050
Gly Ser Leu Lys Tyr Ser Phe Thr Leu Lys Gly Thr Gly Arg Gly
    1055                1060                1065
Asn Ala Pro Val Thr Thr Leu Val Ser Thr Pro Leu Val Arg Gly
    1070                1075                1080
Val Thr Ala Glu Val Asp Asn Ile Thr Val Asn
    1085                1090

<210> SEQ ID NO 4
<211> LENGTH: 570
<212> TYPE: PRT
<213> ORGANISM: Actinoallomurus
```

<220> FEATURE:
<221> NAME/KEY: PROPEP
<222> LOCATION: (1)..(570)

<400> SEQUENCE: 4

Met Arg Arg Ala Leu Val Leu Ala Ala Cys Ala Val Val Thr Ala Ala
1               5                   10                  15

Leu Ala Ala Pro Ala Gln Ala Gly Ser Ser Lys Thr Gln Gly Lys
            20                  25                  30

Thr Thr Glu Tyr Val Val Leu Tyr Lys Asp Gly Val Ser Leu Glu Lys
            35                  40                  45

Ala His Ser Ala Val Lys Ala Gly Gly Thr Ile Val Lys Glu Asn
        50                  55                  60

Lys Ala Ile Gly Val Ala Thr Val Arg Ser Ala Ser Thr Ala Phe Leu
65                  70                  75                  80

Thr Asp Ala Arg Lys Gln Ser Ala Val Asp Gly Val Ala Thr Asn Arg
                85                  90                  95

Ala Val Gly Glu Ala Pro Lys Val Ala Arg Ala Ala Val Asn Lys Ser
            100                 105                 110

Gln Ala Val Glu Lys Glu Gly Arg Val Gly Gly His Ala Gly Ser Ser
        115                 120                 125

Ser His Lys Pro Ser Ala Glu Pro Leu Ala Asp Arg Gln Trp Asp Met
    130                 135                 140

Lys Gln Ile His Ala Thr Thr Asp Gly Ser Tyr Lys Lys Glu Pro Gly
145                 150                 155                 160

Asp Arg Arg Val Leu Val Gly Val Ile Asp Thr Gly Ile Asp Gly Thr
                165                 170                 175

His Pro Asp Ile Ala Pro Asn Phe Asp Lys Ser Leu Ser Arg Asn Phe
            180                 185                 190

Thr Thr Asp Ile Pro Val Asp Ala Asn Gly Thr Glu Val Asp Gly Pro
        195                 200                 205

Cys Glu His Pro Ser Cys Val Asp Pro Val Asp Asp Asp Asn Glu
    210                 215                 220

His Gly Thr His Val Ala Ser Thr Ile Ala Ser Pro Leu Asn Gly Leu
225                 230                 235                 240

Gly Ile Ala Gly Val Ala Pro Asn Val Thr Leu Val Asn Val Arg Ala
                245                 250                 255

Gly Gln Asp Ser Gly Tyr Phe Phe Leu Gln Pro Val Val Asp Ala Leu
            260                 265                 270

Thr Tyr Ser Ala Asp His Gly Ile Asp Val Val Asn Met Ser Phe Tyr
        275                 280                 285

Thr Asp Pro Trp Leu Phe Asn Cys Thr Asn Asn Pro Ala Asp Ser Pro
    290                 295                 300

Glu Asn Gln Ala Glu Gln Arg Thr Val Ile Gln Ala Ser Glu Arg Ala
305                 310                 315                 320

Leu Ala Tyr Ala His Arg His Gly Val Thr Leu Val Ala Ala Ala Gly
                325                 330                 335

Asn Gly Ala Thr Asp Tyr Thr Lys Thr Ile Thr Asp Ala Ser Ser Pro
            340                 345                 350

Asp Tyr Pro Ser Val Pro Gly Glu Ala Pro Tyr Ser Arg Thr Ile Pro
        355                 360                 365

Pro Ser Cys Ile Ser Glu Pro Ser Glu Gly Gln Asn Val Leu Ala Val
    370                 375                 380

Ser Ala Leu Gly Ile Ser Thr Arg Lys Ser Tyr Tyr Ser Asp Tyr Gly

```
                385                 390                 395                 400
Asn Gly Tyr Val Ala Val Ser Ala Pro Gly Gly Asp Ser Tyr Asp Thr
                    405                 410                 415

Ala Asp Gln Lys Ala Asp Val Thr His Ala Ile Leu Ala Ala Tyr Pro
                420                 425                 430

Lys Ser Leu Ala Val Ala Arg Gly Glu Leu Asn Ala Asp Gly Thr Pro
                435                 440                 445

Asn Val Pro Tyr Val Val Arg Ser Cys Lys Gly Ser Thr Cys Ala Tyr
            450                 455                 460

Tyr Gln Tyr Leu Gln Gly Thr Ser Met Ala Ser Pro His Ala Thr Gly
465                 470                 475                 480

Val Val Ala Leu Ile Val Ser Arg Tyr Gly Lys Pro Asp Arg Val His
                485                 490                 495

Gly Gly Leu Thr Leu Ser Pro Asp Arg Val Lys Ser Ile Leu Glu Gly
                500                 505                 510

Thr Ala Thr Glu His Ala Cys Pro Asp Pro Arg Ala Phe Thr Tyr Thr
                515                 520                 525

Arg Gln Val Lys Gln Ser Asp Gly Thr Tyr Arg Thr Val Thr Ala Thr
            530                 535                 540

His Thr Cys Glu Gly Ser Lys Ser His Asn Gly Phe Tyr Gly His Gly
545                 550                 555                 560

Ile Ile Asp Ala Leu Gly Ala Val Thr His
                565                 570

<210> SEQ ID NO 5
<211> LENGTH: 416
<212> TYPE: PRT
<213> ORGANISM: Actinoallomurus
<220> FEATURE:
<221> NAME/KEY: PROPEP
<222> LOCATION: (1)..(416)

<400> SEQUENCE: 5

Met Asn Pro Arg Gln Arg Phe Ala Ile Val Leu Ala Ala Leu Ile Thr
1               5                   10                  15

Met Ile Phe Ser Leu Val Ser Val Pro Ser Ala Gly Ala Ala Val Ser
                20                  25                  30

Ala Ser Lys Leu Ser Val Gly Phe Gly Cys Ala Ser Ala Ala His Ala
            35                  40                  45

Gly Gln Leu His Cys Phe Gly Arg Ile Arg His Arg Ala Ser Asn
    50                  55                  60

Gly Lys Ile Ala Pro Leu Thr Val Thr Ser Pro Thr Gly Leu Leu Pro
65                  70                  75                  80

Ala Asp Leu Gln Ser Ala Tyr Lys Val Ala Gly Leu Asn Gly Gly Gly
                85                  90                  95

Arg Thr Val Ala Ile Val Asp Ala Gln Asp Asn Pro Lys Ala Glu Ala
                100                 105                 110

Asp Leu Ala His Tyr Arg Ser Gln Leu Gly Leu Pro Ala Cys Thr Thr
            115                 120                 125

Ala Asn Gly Cys Phe Lys Lys Val Asn Gln Asn Gly Gln Ala Ser Pro
        130                 135                 140

Leu Pro Ala Ala Asp Tyr Gly Trp Ala Glu Glu Ile Ser Leu Asp Leu
145                 150                 155                 160

Asp Met Val Ser Ala Ile Cys Pro Ser Cys His Ile Leu Leu Val Glu
                165                 170                 175
```

Ala Asn Ala Pro Asp Asp Thr Ser Leu Gly Thr Ala Val Asp Thr Ala
                180                 185                 190

Ala Ala Thr Ser Gly Val Val Ala Ile Ser Asn Ser Tyr Gly Gly Ala
        195                 200                 205

Glu Asp Ser Thr Ile Leu Ala Ala Asp Ala His Phe Asn His Pro Gly
    210                 215                 220

Ile Ala Val Thr Ala Ser Ser Asp Ser Gly Tyr Gly Val Ser Trp
225                 230                 235                 240

Pro Ala Ser Ser Gln Tyr Val Thr Ala Val Gly Gly Thr Leu Asn
                245                 250                 255

Lys Ala Ser Asn Ala Arg Gly Trp Thr Glu Thr Ala Trp Ser Gly Ala
                260                 265                 270

Gly Ser Gly Cys Ser Ala Tyr Glu Pro Lys Pro Ser Trp Gln His Asp
            275                 280                 285

Thr Ala Cys Ala Lys Arg Thr Val Ala Asp Val Ser Ala Val Ala Asp
                290                 295                 300

Pro Ala Thr Gly Val Gly Val Tyr Asp Thr Tyr Asn Ser Cys Gly Thr
305                 310                 315                 320

Ser Ser Phe Cys Asp Phe Leu Ile Ser Leu Gly Leu Val Gln Gly Leu
                325                 330                 335

Asp Gly Trp Ala Ala Val Gly Gly Thr Ser Ala Ser Ser Pro Ile Ile
            340                 345                 350

Ala Ser Val Tyr Ala Leu Ala Gly Asn Thr Gly Ser Thr Thr Tyr Gly
                355                 360                 365

Ser Tyr Pro Tyr Ala His Thr Ser Ala Leu Phe Asp Val Thr Ser Gly
            370                 375                 380

Ser Asn Gly Ser Cys Gly Gly Thr Tyr Leu Cys Thr Ala Gly Thr Gly
385                 390                 395                 400

Tyr Asp Gly Pro Thr Gly Leu Gly Thr Pro Asn Gly Thr Gly Gly Phe
                405                 410                 415

<210> SEQ ID NO 6
<211> LENGTH: 33
<212> TYPE: PRT
<213> ORGANISM: Artificial Sequence
<220> FEATURE:
<223> OTHER INFORMATION: The gliadin 33-mer peptide

<400> SEQUENCE: 6

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
                20                  25                  30

Phe

<210> SEQ ID NO 7
<211> LENGTH: 4173
<212> TYPE: DNA
<213> ORGANISM: Actinoallomurus
<220> FEATURE:
<221> NAME/KEY: gene
<222> LOCATION: (1)..(4173)

<400> SEQUENCE: 7
atgcccgatc ttcccaccca acggcgttcc ccacgcaggt cacgccggcc cgcggtcctt    60
gcgaggctcg cgggcctgcg cgtcggcgcg ctggtcctcg cgctcgccgt caccacgctc   120
accctcatct ccatgccctc ggccaacgcc gccccggcca agcccgtggt cccgcacgcc   180

```
aaggcgagca gtcccaccgc acagggccag cacccgacca gccgcgtgtg ccggacccc    240
ggccgcgcca atgagatgac ctgcctcgcc atggtccgtg acgacgtcat cgggccgaag   300
ggcgtccagg cgaacgacgc gccggccggg ttcggcccgg ccgacctgct gaacgcctac   360
aacctgccct cggccggatc gacgagacg gtcgcgatcg tcgacgcgtt cgacaacccg    420
aacgccgagg cggacctggg cgtctaccgc cagcagtacg ggctgccggc ctgcacgacg   480
gccaacggct gcttcaagaa gatcgaccaa cgcggcggca ccagctatcc gccgccggac   540
gccggctggg ccggagagat cgcgctggac atcgacatgg tcagcgccat ctgcccgacc   600
tgcaagatcc tcctggtcga ggccgacgac aactacatgg acaacctggg cacggccgtc   660
aaccaggcgg tcagccaggg cgccaagttc gtctccaaca gctacggcgg cagtgagggc   720
tccgacgagg ggcaggccga cgacgcgtac ttccaccacg acggcgtcgc catcaccgcg   780
agcagcggcg acagcggcta cggggcgagc tacccggccg cctccccgta cgtcacctcg   840
gtcggcggca cgtcgctggc caaggacacg tcctcctcgc gcggctggac cgagagcacc   900
tggaacggcg cgggcagcgg ctgctccgcg tacgagacca agccctcgtt ccagaaggac   960
accggctgcg cgcgccgtac gatcgccgac gtctccgcgg tggccgaccc gaacaccggc  1020
gtcgcggtct acaacggcgg ctggcacgtc tacgcggca cgagcgtgtc cgccccgatc   1080
atcgcgtcgg tgtacgccct cggcggcgcg ccggcggcgg gctcggcgcc caactccttc  1140
ccgtacgacc acccggccga cctcaacgac gtgaccagcg gcagcaacgg gagctgtagt  1200
cccgcctacc tctgcacggc gggtaccggc tacgacgggc cgaccgggct cggcaccccg  1260
aacggcatcg ccgcgttccg ctccgggccg cacgccgtcg tcaccggtac ggtcaccgac  1320
ggcaccgcgc cgctggcgtc cgcccaggtg aaggcgggcg acgtcacggc gacgacggac  1380
ggccaggggc actacaccct gagcgttccg ccggggacct acgacgtgtc cgcgagcaag  1440
ttcgggtaca ccggtaagac gatctcgggg gtgcaggtcg ccgacggcca gaccgtcacc  1500
gaggacttcg cgctgaccgc caaggcacgc gtcgacgtct ccggactcgt acgggacggc  1560
tcgggtcacg gctggccggt ctacgcgacc gtacgggtca aggaccagcc caccgcggtc  1620
gcctacaccg acccgaagac cgggcggtac accctcagcc tgcccacgga cgacacgtac  1680
acgctgcagg tggatccgct gtatccgggt tacacgcagg actcgcacga cgtgaccgtg  1740
acctcggcgg acgtggtcca cgacgtcaac gtcgcggtgg accagacgac gtgcagcgca  1800
ccgggctaca gctaccacta cgccggagcc acccagccgt tcgacggcac gaccgcgccg  1860
gcgggctgga ccgtcgatga caaggtcggc aacggccaga cctgggtgtt caacgacccg  1920
ggctcccgtg caacaagac gggcgggacc ggcggcttcg ccgtcatcga cagtgaccac  1980
tacggctcgg caacacgca ggacagcacg ctgttcagcc cggtcaccga cttcagcgcg   2040
cgtacccacc cgatcctgag cttccgcagc gactggtacg gctacaccgg ccaggccggc  2100
gacctcgacc tgagcgtcga cggcggcacg acgtggacca acctgaagca ctacacggcc  2160
agcgagcgcg ggccgcgtac ggagacgatg gacctgtccg cggcggccgg gaagagcgcc  2220
gtgcaggtga ggttccactt caccggcaag ttcggctact actggcaggt cgacgacgtc  2280
ttcctcggcg accgtacctg tgacccgacc tcgggcggcc tggtcgtcgg ccaggtgacc  2340
gacgcgaaca ccggcgcggg cgtggccggg gccacggtca cctcggtgga ccggccggcc  2400
gagcacgcca cctcggcggc gacgccggac gaccccaacc tcggcgacgg tctcttctgg  2460
atgttctcct ccgtcaccgg cagccacaag ttcaccgcca cggcggggaa ctacgactcc  2520
```

| | |
|---|---:|
| catgacgtca cggtgaacgt cgccgccaac tgggcgaccg cggccgacat cgcgctgtcc | 2580 |
| gcgccacggc tcacggtcac tccgggcgcg atcagcaaga cggtcggctg cagaaggcg | 2640 |
| gccaccgcgg cgctgaccct gaagaacacc ggcacgtcgc cggtgaccgc caagatcggt | 2700 |
| gaacagccgg gtggcagcac gaccgccacc gcgggtgcac cgctgcagcg ggtgaagggc | 2760 |
| gacttcgcca gtggacgact gcagcagggc aaggcgtcgg gtgccaaggc cggcgtgaca | 2820 |
| ccgtacgcgc cgccgtggac ggccatcgcc gactacgcct cgccgatcat ggacaacggc | 2880 |
| gcggtggcac tgaacggcaa gatctactcg gtggcgggcg tcgacggcgc gaacgtgctg | 2940 |
| aacaaggcgt acgcctacga tcccggcacc caggcctgga ccgccatcgc cccgctcgcc | 3000 |
| acgggacgtg aggctcccca ggcgacgacc accggcggaa agctgtacgt caccggcggc | 3060 |
| tggggctcga cgggcgccgc ggtggccaag acggagatct tcgatccgtc ctcgggcgcc | 3120 |
| tggtcggccg gcgcggacaa cccgaagccg tacgccggct ccggcgcggc cgtgctcgac | 3180 |
| ggcaagatct acgtcgtcgg cgggtgcctc gccacctgcg gtacgaagga cgtgcaggtc | 3240 |
| tacgacccgg cggccaactc ctggagctcg ggaccggcct atccggagaa caccgcgtgg | 3300 |
| ctcggctgcg ccggcatcga cggcaagctg tactgcgcgg gcggctccgc ggccgcgagc | 3360 |
| accaagcacg gctacgtgct cgacccggcc tcggcacctt ggtcgccgat cgccgacctg | 3420 |
| ccgatcgacc tgtgggcgat gggctactcg gcggcgaacg ggaagctgat cgtctccggt | 3480 |
| ggcgtcacca acggggccag cacgctcacc aatcagggct cgcctacga cccgtcggcg | 3540 |
| aactcctgga cggccctgcc caactccaac aacgccctgt accgcggcgc gtcggcctgc | 3600 |
| gggttctaca gatcggagg atcgctgggg cagttcaacg cggtcaagag cggtgaggtg | 3660 |
| ctgcccggct atgaccagtg cgcctcgacc gccgacgttc cgtggctgtc ggaggacaag | 3720 |
| accgaggtga cgatccagcc cggccagagc gtcaaggtca acgtgaccct cgacgcgaac | 3780 |
| gtcccggcga tcactcagcc cggcacgtac accgcgcagc tcaccgtcgg ggcgaagacg | 3840 |
| ccgtacgcga tcccgccggt cgccgtcacg atgacggtga accgccgggg cacctggga | 3900 |
| aagatcaccg gaacgctcac cggagccggc tgtacgggtt ctcccgcacc gctgaccggg | 3960 |
| gcgaccctac agatcgactc ctgggctgcg tcgtacacgc tcaagaccga caagaacggt | 4020 |
| cagtacgcgc tctggctcga cgtccgcaac aacccgctga cgctgatcgc ggcgaaggac | 4080 |
| ggatgggcgc cgcagaccag aaacgtcaag atcaccaaac tgacctcgac cacggccgat | 4140 |
| ttcactctga aacccgacca cacctgtagc tga | 4173 |

<210> SEQ ID NO 8
<211> LENGTH: 1197
<212> TYPE: DNA
<213> ORGANISM: Actinoallomurus
<220> FEATURE:
<221> NAME/KEY: gene
<222> LOCATION: (1)..(1197)

<400> SEQUENCE: 8

| | |
|---|---:|
| atgtcacgac gcgtgaccgg gaccatactg ggcgggttga tcctcgccat ggtccccttc | 60 |
| ctttccaccg cggccaacgc cgcacccag gccgcgccgg cttccgtctc ccacccgttc | 120 |
| caccactcct gcgccacggt gaagccgggt cgggcgagct gcaatgccct cgtacgcagc | 180 |
| gacatcgccc agagcgcggc gaccctcgcg caccaagcgg ccgccccatc cgggctctcg | 240 |
| ccggccaacc tgcagagcgc ctacaagctg ccgtcctcca cggccggatc cggccagacc | 300 |
| gtcgcgatcg tcgacgccta tgacgccccg accgccgaag cggacttgaa cgtgtaccga | 360 |

| | |
|---|---|
| agccagttcg gactcggcgc gtgcacgacc gccaacggct gtttcaagaa ggtcgaccag | 420 |
| aacggcggca cgtcctatcc gaggaaggac ggcggctggg cgcaggagat ctccctggac | 480 |
| ctcgacatgg tctccgcggt ctgccccaac tgcaagatcg ttctcgtcga ggcgaagacc | 540 |
| aactcgttcg ccaacctggg taccgccgag aacaccgcgg cgagtctcgc gaacgtcatc | 600 |
| agcaacagct acggcggctc ggacgcctct gacgcgagct atggctcgta ctacaaccac | 660 |
| ccgggcaagg ccatcacggt cagctccggc gacgccggct acggcgtgga gtacccggcc | 720 |
| tcgtcccact acgtgaccgc cgtcggcggc acctcgctgc gcaccgcgag caccagccgc | 780 |
| ggctggagcg agaccgcgtg gagcggcgcg ggcagtggcg gctcggccta caacaccgcg | 840 |
| ctgtccggcc agtccggcct caccggctgc tcccggcgcg ccgtcgccga cgtctccgcc | 900 |
| gtggccgacc cggccaccgg cgtcgccgtc tacgacagca cggcctacca gggccagagc | 960 |
| ggctggatgg tcttcggcgg caccagcgtc gccgcaccga tcatcggtgg cgtgtacggc | 1020 |
| ctcgccgcca acgccgcgag catcgacaac aactacccct acgccacaca cagctcgctc | 1080 |
| ttcgacgtca cgtcgggcag caacggcacc tgcaccacca ccaagtggtg caccgccggc | 1140 |
| accggctggg acggccccac cggcctcgga acgccgaacg cgaccggagc cttctga | 1197 |

<210> SEQ ID NO 9
<211> LENGTH: 3285
<212> TYPE: DNA
<213> ORGANISM: Actinoallomurus
<220> FEATURE:
<221> NAME/KEY: gene
<222> LOCATION: (1)..(3285)

<400> SEQUENCE: 9

| | |
|---|---|
| atgagtgccg ccgttgtgat cttcgccggc gcaccggcga cggcggcgcc gacgccggaa | 60 |
| ggctccggca gacactggac ggccacgccg ctcagcggca ccgtcgtcca gggcttcaag | 120 |
| tcgacgaccg gacggctcgc caagagcgat gccgggctgc ttcgcctgaa gtcgagcaag | 180 |
| cccgtgcacg tcatggtcaa gctcgactac gactcactcg ccgcctaccg gggcgggatt | 240 |
| cccgggtacg ccgccacgag cccggcggtg accgggcaca cgctcgaccc ggcgagcgcc | 300 |
| ggcgcgcggc gctaccaggg ctacatcggg ggcgtcgaga accgcttccg cgccgccctg | 360 |
| ggcaagcgcc tgccgggcgc gaaggccggc ggcgggctgc gcacggtgta cggcggtctg | 420 |
| gcggtgacgc tgcccggtga caaggtggcc gacctgctca gctgcccggc gtggccgcg | 480 |
| gtccaggagg acgcggtggc caagccactg accgactcca gccccggctt catcggcgcc | 540 |
| ccgaccatct acaagcaact cggcggcagc gacagctccg gaaagggcgt catcgtcggc | 600 |
| gacctggaca gcggcgcctg gcccgagcac ccctcgtaca aggacagcgg caagctgccc | 660 |
| gcgccgccgc ccaccacgga cggtgcgcca cggccgtgcc acttcggcga caatccgctg | 720 |
| acgccggcga acgacccgta cgtctgcgac cacaagctga tctcgggcca gccgttcctg | 780 |
| gacacctaca acgcggtcgt cggcgggag aggttccccg cagcgcccg cgactccgac | 840 |
| gggcacggca cgcacaccct cgaccaccgc gccggttcgg cggtgagcca cgcgaacccg | 900 |
| ctcggcatcg accgcggcgc catccacggc atcgcgcccg ccgcccacat cgccgtctac | 960 |
| aaggtgtgcg cgcccagggg ctgcttccag tccgactcgg tggccgccgt gcagcgggcg | 1020 |
| atcctcgaca aggtccgggt gatcaactac tcgatctccg gcgcgtcga cccatacagc | 1080 |
| gatccggtcg aactggcctt cctcgacgcg tacgcggccg gcgtgctcgt ctcggcctcg | 1140 |
| gccggcaacg acgggcccac cgcgggcacc gtcaaccaca acgggccgtg ggtgaccacg | 1200 |

-continued

```
gtggccgcgt ccacgcagca gcggaccttc cagtcgaccg tcacgctgca ggcgggcggc    1260
gcgagcctga agctggccgg ctcgtcgatc accagcggga tcacctcgcc gcttcccgtc    1320
gtgctcgcgt ccgcggcgcc gtacggcgac ccggactgtg acacgcaggc cgctcccggc    1380
acgttcaccg gcaagatcgt cgcctgccgg ctgctcaacc gcggccggat catgaagggc    1440
tacaacgtct tcaagggcgg cgcggccggg atgctgctct acaacgacac gctgtcccag    1500
acgatgaccg acaaccactg gctgccgacc gtgcacctgg agaagccgca ggccgacgcg    1560
ctgctggcct tcctttccgg ccacaccggc accaccgcca cgttccccca gggcgcgaag    1620
gcgaacggcc agggcgacgt catgaccgcg ttctcctcgc gcggcccggg cggcgacttc    1680
ctcaagcccg acgtcaccgc gcccggcctg cagatcatgg gcggccagac gccggttccg    1740
gacgacccct cgctgggccc gcccggcacc ctctaccagg tgatcgccgg tacctcgatg    1800
tcggcgccgc acgtcaccgg ggcggcggcg ctgctgttcg ccctgcatcc gagctggacg    1860
ccggggcagg tcaagtcggc gctggagacg accggcaaga cgtctgtggt caagcacgac    1920
cgcaagacgc ccgccgaccc gttcgacctc ggcggtgggc gcatcgacct caccaaggcc    1980
ggtgaccccg ggctgaccat cgacgagacc gcggcgaact acgcggcctc ggcgaccgac    2040
ccgctgcacc ggatcgacct gaacgtgccg tctgtgaacg caccggtgat gcccggcgcg    2100
atcatgacca cccgtacggt caagaacgtc tcgggaaaga cgatgacgta cggcacctcg    2160
ggtacgacgg tgaagggcgc ctccatctcc gtctcccccg gcacgttcac cgtcaagccg    2220
ggcaagaccg cccggctgcg gatcacgatc gccgcgccgg cgctcgccaa tgggcagtac    2280
ttcggccggg tcgacctgcg tcagcgaaac ggcggccacg acctgcacct gccggtcgcg    2340
ttcgtccgca agcagggcgt ggtgagcctg aaccagacct gcacgccctc ggtgatcgcg    2400
ctgaacagcg gccgatcgac gtgcgacgtc gacgtcgaga cacctctctc cgccgacacc    2460
aaggtcatcg ccgcgagcca cctggacacg cggctgcgac tgaccgcggt gaccggcgcg    2520
acgaaggtgg gcgcgcacga cgtcctggcc caggccgacc tggcccgccg ccagcccgac    2580
aagccgcaga tcgcccccgg ggccacgccg gccggctacc tgccgctcga cgccttcggc    2640 atcccccga gccgatcgg cgacgagcag tcgctcaacc tcaccacgcc ggcgttcacc    2700
ttcgccggca ggacctacac cagcctgggc gtggtctccg acggctacac ggtcgccggc    2760
ggagcgaccc ccgatgacgt ggccgcgacg ccgcagaccc tgccgaaccc ggcacggccg    2820
aacggcgaac tggccccgtt ctggaccgac ctggacggcg ccggtgcccc gggcgtgtac    2880
gcggcccgcc tcaccgacgg cacgagcacc tggatcgtcg tggagtggcg gctcaacgtc    2940
ttcggcacga acagcctccg ggtgttccag cagtggatcg gggtgaacgg cgccgaggac    3000
atctcctaca cctacgaccc gaacaacctg cggcggcgc cgcccgcggg ctacggcctg    3060
acggtcggcg cggagaacga cgagggtacc gccggttcgc agatctccgg caccccgacc    3120
gaggatctcc gcgtcacgag cacgccgggg gccgcgggtg gttcgctgaa gtactccttc    3180
acactgaagg gaacgggccg gggcaacgcc ccggtgacga ccctggtctc cacgccgctc    3240
gtacgaggcg tgacggccga ggtcgacaac atcacggtga actga                   3285
```

<210> SEQ ID NO 10
<211> LENGTH: 1713
<212> TYPE: DNA
<213> ORGANISM: Actinoallomurus
<220> FEATURE:
<221> NAME/KEY: gene
<222> LOCATION: (1)..(1713)

<400> SEQUENCE: 10

```
gtgcggcgcg ccctagtcct cgccgcctgc gccgtcgtca cggcggcgct cgcggcaccc      60
gcgcaggcgg gatcgagcag caagacgcag ggaaagacga ctgagtacgt cgtcctgtac     120
aaggacggag tctccctgga gaaggcgcac tcggccgtga aggcggccgg tggcaccatc     180
gtcaaggaga caaggcgat cggcgtggcc accgtacgct cggccagcac ggcgttcctc      240
accgacgcgc gcaagcagtc ggcggtcgac ggcgtcgcga ccaaccgcgc ggtcggcgag     300
gcgcccaagg tcgcacgggc ggcggtgaac aagagccagg ccgtggagaa ggagggccgc     360
gtcgggggcc atgcggggtc ctcctcgcac aagccgtcgg cggagccgct ggcggaccgt     420
cagtgggaca tgaagcagat ccacgcgacc acggacggct cgtacaagaa ggagccgggc     480
gaccggcgcg tgctcgtcgg cgtcatcgac accggcatcg acggcacgca cccgacatc     540
gcgccgaact tcgacaagtc gctgagccgg aacttcacca cggacatccc ggtcgacgcc     600
aacggcaccg aggtcgacgg cccgtgtgag caccgtcct gcgtggaccc ggtggacgag      660
gacgacaacg agcacggcac gcacgtcgcc tcgacgatcg cctcgccgct gaacggcctg     720
ggcatcgcgg gcgtggcgcc gaacgtgacg ctggtcaacg tacgggccgg gcaggactcg     780
ggctacttct tcctgcagcc cgtggtcgac gcgctgacgt actcggccga ccacggcatc     840
gacgtggtga acatgtcgtt ctacaccgac ccgtggctgt tcaactgcac caacaacccg     900
gccgactcgc cggagaacca ggccgagcag cgtacggtca tccaggcgtc agaacgcgcc     960
ctggcgtacg cgcaccggca cggtgtcacc ctggtggcgg ccgccggcaa cggcgccacc    1020
gactacacca agacgatcac cgacgcgtcg agcccggact accgtccgt gcccggcgag    1080
gcgccgtact cgcgtacgat cccgccgtcc tgcatctccg agccgagcga gggccagaac    1140
gtcctcgcgg tgtcggccct gggcatcagc acgcgcaagt cgtactactc cgactacggc    1200
aacggctacg tcgcggtgtc ggccccgggc ggcgactcct acgacacggc cgaccagaag    1260
gcggacgtga cccacgcgat cctggccgcg tacccgaagt ccctggccgt ggcccgcggc    1320
gaactgaacg cggacggcac cccgaacgtg ccgtacgtgg tccgctcgtg caagggctcg    1380
acctgcgcgt actaccagta cctgcagggc acgtcgatgg cctctccgca cgcgaccggc    1440
gtggtggcgc tgatcgtcag ccgctacggc aagcccgacc gcgtacacgg cggcctgacc    1500
ctgtccccgg accgggtcaa gtccatcctg gagggaaccg ccaccgaaca cgcctgcccg    1560
gacccacgcg ccttcacgta cacgcgccag gtcaagcagt ccgacggtac gtacaggacc    1620
gtgaccgcga cccacacctg tgagggttcg aagagccaca cggcttcta cggccacggc    1680
atcatcgatg ccctgggcgc cgtgacgcat taa                                 1713
```

<210> SEQ ID NO 11
<211> LENGTH: 1251
<212> TYPE: DNA
<213> ORGANISM: Actinoallomurus
<220> FEATURE:
<221> NAME/KEY: gene
<222> LOCATION: (1)..(1251)

<400> SEQUENCE: 11

```
ttgaaccccc gccaaagatt cgcgatcgtc ctcgcggccc tcatcacaat gatcttctcc      60
ctggtttccg tcccctccgc cggcgccgcg gtcagcgcgt ccaagctcag cgtcggcttc     120
ggctgcgcct cggcggcgca cgccggtcag ctgcactgct tcgggcggat ccgcgcccac     180
cgggcgagca acggcaagat cgccccgctc acggtcacca gcccgaccgg actgctcccg     240
```

```
gcggacctgc agtcggcgta caaggtggcc gggctgaacg gcggcggccg tacggtcgcg      300
atcgtcgacg cgcaggacaa cccgaaggcc gaggccgacc tcgcccacta ccgctcccag      360
ctcggcctgc ccgcgtgcac gaccgcgaac ggctgcttca agaaggtcaa ccagaacggc      420
caggcgtcgc cgctgcccgc ggccgactac ggctgggccg aggagatcag cctcgacctg      480
gacatggtct cggcgatctg cccgagctgc cacatcctgc tcgtcgaggc gaacgcccct      540
gacgacacct cgctcggcac cgcggtcgac accgccgccg cgaccagcgg cgtcgtggcc      600
atctccaaca gctacggagg cgccgaggac tcgaccatcc tcgccgccga cgcccacttc      660
aaccacccgg gcatcgcggt cacggcgagc tccggcgact ccggctacgg cgtcagctgg      720
ccggcctcgt cccagtacgt caccgcggtg ggcggcacga cgctgaacaa ggcgagcaac      780
gcgcgcggct ggaccgagac cgcctggtcc ggcgccggct cgggctgctc ggcgtacgag      840
ccgaagccgt cctggcagca cgacaccgcc tgcgccaagc gcaccgtcgc ggacgtctcg      900
gcggtcgccg acccgccac cggcgtcggc gtctacgaca cctacaacag ctgcgggacc       960
agctcgttct gcgacttcct catctcgctc gggctcgtgc agggcctgga cggctgggcc     1020
gcggtcggcg gacgagcgc gtcctcgccg atcatcgcga gcgtgtacgc cctggccggc      1080
aacaccggca gcacgacgta cggctcgtac ccgtacgcgc acacgtccgc gctcttcgac     1140
gtcacgtccg gctcgaacgg aagctgtggc ggcacctacc tgtgcacggc cggaaccggc     1200
tacgacggtc ccaccggtct gggcacgccc aacggaaccg gcggcttctg a              1251
```

<210> SEQ ID NO 12
<211> LENGTH: 28
<212> TYPE: DNA
<213> ORGANISM: Artificial Sequence
<220> FEATURE:
<223> OTHER INFORMATION: PCR primer forward for Endopep140
<220> FEATURE:
<221> NAME/KEY: primer_bind
<222> LOCATION: (1)..(28)

<400> SEQUENCE: 12
aaaaagcttc agctacaggt gtggtcgg                                          28

<210> SEQ ID NO 13
<211> LENGTH: 29
<212> TYPE: DNA
<213> ORGANISM: Artificial Sequence
<220> FEATURE:
<223> OTHER INFORMATION: PCR primer reverse for Endopep140
<220> FEATURE:
<221> NAME/KEY: primer_bind
<222> LOCATION: (1)..(29)

<400> SEQUENCE: 13
aaaaaaacat atgcccgatc ttcccaccc                                         29

<210> SEQ ID NO 14
<211> LENGTH: 26
<212> TYPE: DNA
<213> ORGANISM: Artificial Sequence
<220> FEATURE:
<223> OTHER INFORMATION: PCR primer forward for Endopep40
<220> FEATURE:
<221> NAME/KEY: primer_bind
<222> LOCATION: (1)..(26)

<400> SEQUENCE: 14
aaaaagcttc agaaggctcc ggtgcc                                            26

<210> SEQ ID NO 15
<211> LENGTH: 29
<212> TYPE: DNA
<213> ORGANISM: Artificial Sequence
<220> FEATURE:
<223> OTHER INFORMATION: PCR primer reverse for Endopep40
<220> FEATURE:
<221> NAME/KEY: primer_bind
<222> LOCATION: (1)..(29)

<400> SEQUENCE: 15
aaaaaaacat atgtcacgac gcgtgaccg                                    29

METHOD OF TREATING GLUTEN INTOLERANCE BY MEANS OF NEW S8/S53 ENDOPETIDASES FROM THE ACTINOMYCETE *ACTINOALLOMURUS*

This U.S. Non Provisional application is a divisional application of U.S. patent application Ser. No. 14/356,122 filed on May 2, 2014 which is a U.S. National Stage of PCT/EP2012/071816 filed on Nov. 5, 2012, which claims priority to and the benefit of European Patent Application Ser. No. 11425291.9 filed on Dec. 6, 2011, the contents of which are all incorporated herein by reference in their entireties.

FIELD OF THE INVENTION

The present invention relates to a novel endopeptidase family having unique catalytic properties that render it able to degrade large polypeptides, including those rich in proline. The present invention further relates to methods for producing the enzyme composition as well as pharmaceutical composition and a food supplement containing the enzyme composition and its use in the degradation of polypeptides.

BACKGROUND OF THE INVENTION

Celiac Disease (CD) is a chronic gastrointestinal tract disorder in which ingestion of gluten, present in food products made from wheat, rye, barley and their cross-related varieties, leads to damage of the small intestinal mucosa by an autoimmune mechanism in genetically susceptible individuals (Green P. H. R., Cellier C. "Celiac Disease" N. Engl. J. Med., 2007, 357, 1731-1743; Kagnoff M. F. "Celiac disease: pathogenesis of a model immunogenetic disease" J. Clin. Invest., 2007, 117, 41-9). Mechanisms through which gluten induces its pathogenic effects have been explained in recent years. Both innate and adaptive immunity mechanisms are involved and are responsible for the ultimate mucosal damage.

Gluten consists of gliadins and glutenins, the water/salt insoluble fractions of storage proteins present in cereal grains. A gluten network is created by interaction between the two proteins when flour and water are mixed in the preparation of dough.

Once ingested, gluten goes towards a partial digestion by gastric-pancreatic and brush-border proteolytic enzymes which results in many peptides of different length (few to more than 30 aminoacids) which are resistant to further digestion due to the high content of proline residues as many proteases are unable to cleave peptide bonds located at N— or C-termini of proline (Hausch F., Shan L., Santiago N. A., Gray G. M., Khosla C. "Intestinal digestive resistance of immunodominant gliadin peptides". Am. J. Physiol. Gastrointest. Liver Physiol., 2002, 283, 996-1003; Shan L., Molberg O., Parrot I., Hausch F., Filiz F., Gray G. M., Sollid L. M., Khosla C. "Structural basis for gluten intolerance in celiac sprue" Science, 2002, 297, 2275-2279). The lack of proline-specific cleaving enzymes is not a specific enzyme deficiency in celiac subjects, as suggested in the past, but is proper of the mammalian digestive apparatus which has not evolved to consume proteins with so high proline content in its diet.

Undigested gluten peptides can pass the epithelial barrier through mechanisms not yet clearly explained, although a zonulin-mediated paracellular passage and a transcellular way, transcytosis and retrotranscytosis, have been recently proposed (Drago S., El Asmar R., Di Pierro M., Grazia Clemente M., Tripathi A., Sapone A. Thakar M., Iacono G., Carroccio A., D'Agate C., Not T., Zampini L., Catassi C., Fasano A. "Gliadin, zonulin and gut permeability: Effects on celiac and non-celiac intestinal mucosa and intestinal cell lines" Scand. J. Gastroenterol., 2006, 41, 408-19; Schumann M., Richter J. F., Wedell I., Moos V., Zimmermarm-Kordmann M., Schneider T., Daum S., Zeitz M., Fromm M., Schulzke J. D. "Mechanisms of epithelial translocation of the alpha(2)-gliadin-33mer in coeliac sprue" Gut, 2008, 57, 747-754; Matysiak-Budnik T., Moura I. C., Arcos-Fajardo M., Lebreton C., Ménard S., Candalh C., Ben-Khalifa K., Dugave C., Tamouza H., van Niel G., Bouhnik Y., Lamarque D., Chaussade S., Malamut G., Cellier C., Cerf-Bensussan N., Monteiro R. C., Heyman M. "Secretory IgA mediates retrotranscytosis of intact gliadin peptides via the transferrin receptor in celiac disease" J. Exp. Med., 2008, 205, 143-154).

Once in the lamina propria (LM), deamidation of glutamine to glutamate residues by tissue transglutaminase (tTG, the autoantigen in CD) reinforces their presentation to DQ2 or DQ8 CD4+ T cells (Molberg O., McAdam S., Lundin K. E. Kristiansen C., Arentz-Hansen H., Kett K., Sollid L. M. "T cells from celiac disease lesions recognize gliadin epitopes deamidated in situ by endogenous tissue transglutaminase" Eur. J. Immunol., 2001, 31, 1317-23) producing a pro-inflammatory response with interferon-gamma (IFN-γ) as main cytokine effector. Several gluten peptides have also been shown to cause mucosal damage independently from a specific recognition by CD4+ T-lymphocytes, but inducing an innate immune response by up-regulating the expression of IL-15, cyclo-oxygenase-2 and the activation markers CD25 and CD83 in LM mononuclear cells: among them, the best characterized are peptides p31-43/49 of the α1-gliadins (ePGQQQPFPPQQPY/PQPQPF) (Ciccocioppo R., Di Sabatino A., Corazza G. R. "The immune recognition of gluten in coeliac disease" Clin. Exp. Immunol., 2005, 140, 408-16).

CD is estimated to affect about 1% of both European and North American population, with a study from Finland showing increasing rates (1:47) in elder people (Vilppula A., Kaukinen K., Luostarinen L., Krekelä I., Patrikainen H., Valve R., Mäki M., Collin P. "Increasing prevalence and high incidence of celiac disease in elderly people: a population-based study" BMC Gastroenterol., 2009, 29, 9-49). However, many studies indicate that CD is diffused all over the world with similar prevalence values (Barada K., Bitar A., Mokadem M. A., Hashash J. G., Green P. "Celiac disease in Middle Eastern and North African countries: a new burden?" World J. Gastroenterol., 2010, 16, 1449-57; Dalgic B., Sari S., Basturk B., Ensari A., Egritas O., Bukulmez A., Bans Z., Turkish Celiac Study Group "Prevalence of celiac disease in healthy Turkish school children" Am. J. Gastroenterol., 2011, 106, 1512-7; Makharia G. K., Verma A. K., Amarchand R., Bhatnagar S., Das P., Goswami A., Bhatia V., Ahuja V., Datta Gupta S., Anand K. "Prevalence of celiac disease in the northern part of India: a community based study" J. Gastroenterol Hepatol., 2011, 26, 894-900; Wang X. Q., Liu W., Xu C. D., Mei H., Gao Y., Peng H. M., Yuan L., Xu J. J. "Celiac disease in children with diarrhea in 4 cities in China" J. Pediatr. Gastroenterol. Nutr., 2011, 53, 368-70). No therapies are available at this time and the only remediation to disease is a strict, lifelong gluten-free diet necessary to prevent not only CD specific mucosal damage and consequent malabsorption-related disorders (like iron-deficient anemia or osteoporosis) but also other autoimmune diseases which have been associated with CD, like type 1 diabetes and autoimmune thyroiditis, or heavier complications like enteropathy-associated T-cell lymphomas.

Total avoidance of gluten (safe gluten intake threshold is generally indicated in 50 mg/day, although 10 mg/day is considered more safe) maintains CD in remission in all but a small percentage of patients (2-5%) which suffer of a non-responsive form. Such a diet is, however, strongly demanding for patients, which are restricted in their common activities and suffer from social isolation. The use of gluten as additive in food processes is widespread and is the main cause of unaware ingestion of gluten, making this diet really difficult to maintain.

For these reasons it would be strongly welcome by CD patients any alternative allowing them to assume in their daily diet at least minimal amounts of gluten.

The use of exogenous proteolytic enzymes for gluten detoxification is one of the most promising strategies for CD treatment. Different ways of application can exploit these enzymes potential: treatment of gluten containing flours, before or during dough fermentation, thus going towards the production of "novel food", as well as concomitant consumption of gluten and suitable proteolytic enzymes, thus going as "food supplement", similarly to the use of lactase for lactose intolerance. Necessarily, different enzyme properties are requested to meet the different objectives.

The enzymatic approach for CD treatment is based on the demonstration by Shan et al. (Science, 2002) of microbial enzymes' ability to cleave gluten peptides on specific residues and remove toxic/immunotoxic specific peptide sequences. In particular, they showed that an exogenous prolyl-specific endoprotease derived from *Flavobacterium meningosepticum* (FM-PEP) resulted helpful in the digestion of gliadin peptides. The addition of a PEP either in vitro in the presence of brush border membrane (BBM) extracts or during in vivo perfusion of rat small intestine caused a rapid degradation of the immunodominant 33-mer peptide ("33-mer") and a loss of its capacity to stimulate gliadin-specific T-cells (Hausch et al., 2002).

Other enzymes of the same family (EC. 3.4.21.26) from other bacterial strains (i.e. *Sphingomonas capsulata* and *Myxococcus xanthus*) have been evaluated for this aim by the same authors (Shan L., Marti T., Sollid L. M., Gray G. M., Khosla C. "Comparative biochemical analysis of three bacterial prolyl endopeptidases: implications for coeliac sprue" Biochem. J., 2004, 383, 311-318), Globally, these studies showed substantial differences among the three enzymes with respect to chain-length and subsite specificity and confirmed the potential of oral enzyme therapy, although raised concerns regarding their possible efficacy in-vivo, due to restrictions on substrates specificity, pH of activity (optimal activity at almost neutral pH instead of acidic pH as needed to act in the stomach), long time necessary to complete the digestion of toxic peptides and resistance to degradation by pepsin. A combination of two enzymes with gastric activity and complementary substrate specificity was then suggested (Gass J., Bethune M. T., Siegel M., Spencer A., Khosla C. "Combination enzyme therapy for gastric digestion of dietary gluten in patients with celiac sprue" Gastroenterology, 2007, 133, 472-480): PEP from *S. capsulata* associated to EP-B2, the glutamine-specific endoprotease B isoform 2 from *Hordeum vulgare*, a cysteine-protease derived from germinating barley seeds that is activated at acidic pH and by pepsin (Bethune M. T., Strop P., Tang Y., Sollid L. M., Khosla C. "Heterologous expression, purification, refolding, and structural-functional characterization of EP-B2, a self-activating barley cysteine endoprotease" Chem. Biol., 2006, 13, 637-47), showed to be a potentially more potent therapeutic tool. Another study reports that a PEP derived from *Aspergillus niger*, deploying its main activity under acid conditions in the stomach, can start to degrade gliadin before it reached the intestinal lumen (Stepniak D., Spaenij-Dekking L., Mitea C., Moester M., de Ru A., Baak-Pablo R. van Veelen P., Edens L., Koning F. "Highly efficient gluten degradation with a newly identified prolyl endoprotease: implications for celiac disease" Am. J. Physiol. Gastrointest. Liver Physiol., 2006, 291, G621-9).

These findings have been dealt by several patent documents. In WO2003/068170 (EP572127), inventors claim that administering an effective dose of glutenase to a celiac or dermatitis herpetiformis patient reduces levels of toxic gluten oligopeptides, thereby attenuating or eliminating the damaging effects of gluten. Further support to this approach is given in WO2005/107786 (EP1740197), where pharmaceutical formulations of glutenase enzymes for use in the treatment of celiac or dermatitis herpetiformis patients are disclosed. WO2005/027953 (EP 16663298) describes a treatment with a new prolyl-specific endoprotease from *Aspergillus niger* (AN-PEP) which resulted helpful in digestion of toxic gluten peptides. WO2005/019251 provides leucine aminopeptidase (LAP) of two different fungal species, *Trichophyton rubrum* and *Aspergillus fumigatus* in combination with dipeptidyl peptidase IV (DppIV). These enzymes have been evaluated for cleavage of the 33-mer under neutral pH conditions since the optimal activity of LAPs was estimated around 7.0 with a range of activity between pH 6 and 8, thus precluding or limiting a possible breakdown of gliadin in the gastric fluid.

It has also been shown that *A. fumigatus* tripeptidyl peptidases can degrade proteins at acidic pH (Reichard U., Lechenne B., Asif A. R., Streit F., Grouzmann E., Jousson O., Monod M. "Sedolisins, a new class of secreted proteases from *Aspergillus fumigatus* with endoprotease or tripeptidyl-peptidase activity at acidic pHs" Appl. Environ. Microb., 2006, 72, 1739-48). In WO2011/077359 it is provided a kit composed by a prolyl-protease (AfuS28) and at least one tripeptidyl protease belonging to the family of sedolisin to be used as food supplement useful also for CD treatment.

It is clear that the therapeutic value of an enzyme or enzyme composition for CD treatment is related to the enzymes a) being resistant to degradation by other gastrointestinal enzymes, b) being efficient in the environment where 33-mer and the others toxic peptides are produced, and c) exhibiting rapid and high proteolytic activity toward gluten peptides. These enzymes should be active at acidic pH and should be able to access a complex composition of gluten hindered by other components of normal foodstuffs baked or cooked.

SUMMARY OF THE INVENTION

The Applicants in the present invention have identified a new family of enzymes and provide an enzyme or a composition of this enzyme family having unique catalytic properties.

The Applicants have identified an *Actinoallomurus* sp. as producer of this enzyme family. The endopeptidases of the invention are produced by cultivation of *Actinoallomurus* in an appropriate culture medium, for example containing soya. The strain, originally identified with the Applicant code A8, was isolated from an Italian soil and deposited on Jun. 24, 2011, with the DSMZ-Deutsche Sammlung von Mikroorganismen und Zellkulturen GmbH, (now Leibniz-Institut DSMZ-Deutsche Sammlung von Mikroorganismen und Zellkulturen GmbH), Inhoffenstarsse 7b, D-38124

Braunschweig, Germany, under the provision of the Budapest Treaty. The strain was accorded accession number DSM 24988.

The endopeptidases of the present invention are able to hydrolyze certain gluten oligopeptides, which are resistant to cleavage by gastric and pancreatic enzymes and whose presence in the intestinal lumen results in toxic effects. The enzymatic treatment can remove such peptides and their toxic effects; it can degrade gliadin and so detoxify gluten without any PEP addition. The peptidases of the invention have a wide range of pH activities and are able to exert proteolytic activity from pH3 to pH8. Such activity will be defined as glutenase activity.

These glutenase enzymes provide methods for preventing the symptoms of Celiac Sprue and/or dermatitis herpetiformis by decreasing the levels of toxic gluten oligopeptides in foodstuffs, either prior to or after ingestion by a patient. These enzymes can be used together with other proteolytic enzymes such as proteinases and aminopeptidases to effectively produce protein hydrolyzates used for foods and drinks, and medicines.

These enzymes are secreted by different *Actinollomurus* strains by cultivating them in suitable media and their activity can be evaluated by using both chromogenic substrates and zymographic analysis.

Furthermore, the enzymes of the invention can be produced into host cells by introducing a nucleic acid encoding for these enzymes, cultivating the cells in a culture medium under conditions suitable for producing and recovering the enzymes.

Protein sequences were aligned with CLUSTALW program and the maximum likelihood tree with bootstrap values was calculated using MEGA5 software. *Actinoallomurus* sp. endopeptidases are in bold. SedE was used as outgroup. The tree was then visualized with MEGA5 software. Bootstrap values equal or higher than 50% are indicated at nodes. The scale bar indicates the number of amino acid substitutions per site.

SedE=sedolisin E from *A. fumigatus* Af293 (EAL86850); SedB=sedolisin B from *Aspergillus fumigatus* Af293 (CAE17674); TPPa=tripeptidyl peptidase A from *A. oryzae* RIB40 (BAC56232); SedD=sedolisin D from *A. fumigatus* Af293 (CAE17675); SedC=sedolisin C from *A. fumigatus* Af293 (CAE46473); SedA=sedolisin A from *A. fumigatus* Af293 (CAE51075); KumaA=Kumamolisin-As from *Alicyclobacillus sendaiensis* (Q8GB88); KumaB=Kumaniolisin from *Bacillus* sp. MN-32 (Q8RR56); sedolisinA=sedolisin from *Pseudomonas* sp. 101 (P42790); sedolisinB=sedolisin-B from *Xanthomonas* sp. T-22 (Q60106); Endopep- are the glutenases of the invention. Protein sequence accession numbers are reported in brackets.

Figure 2:
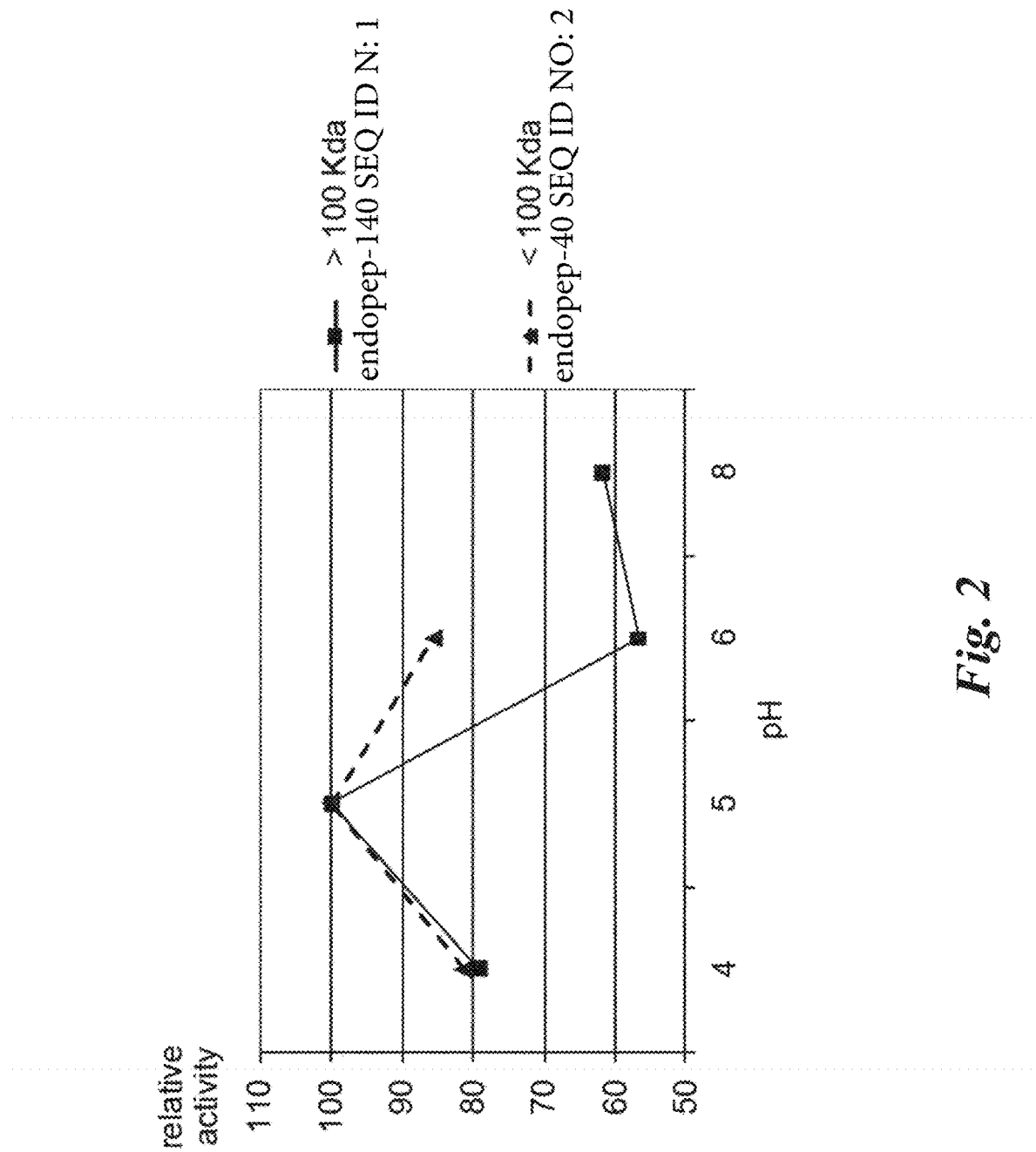

FIG. 2: Activity profile of endopep-140 (>100 kDa) and endopep-40 (<100 kDa) measured on the fluorescent substrate Succinyl-Ala-Ala-Pro-Phe-AMC under various pH conditions. Fluorescence measured after 2 h at 37° C. Specific pH values are given on X-axis, percentage of relative activity on Y-axis.

Figure 3:
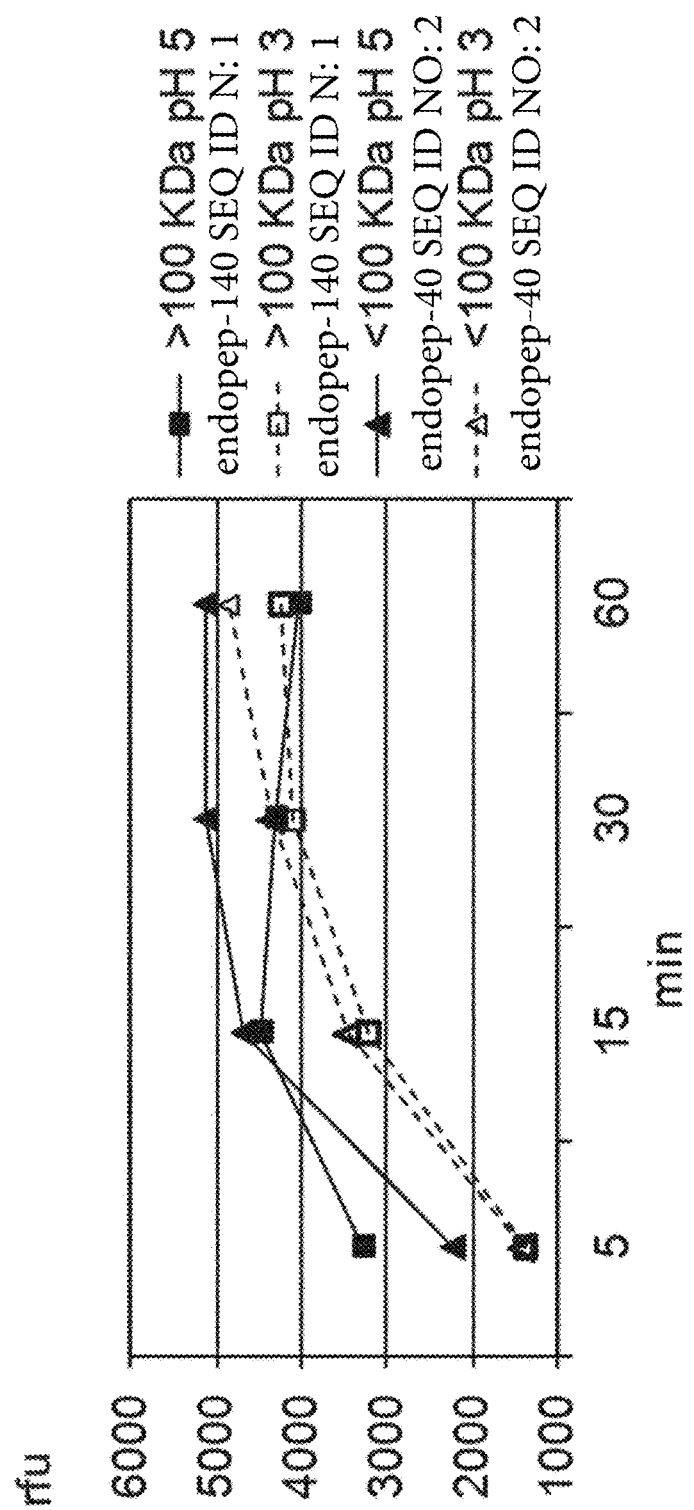

FIG. 3: Endopeptidase activity of endopep-140 (>100 kDa) and endopep-40 (<100 kDa) measured on the fluorescent substrate Succinyl-Ala-Ala-Pro-Phe-AMC at pH3 and pH5. Fluorescence measured at various time intervals at 37° C. Incubation times are given on X-axis, arbitrary fluorescence units (rfu) on Y-axis.

Figure 4:
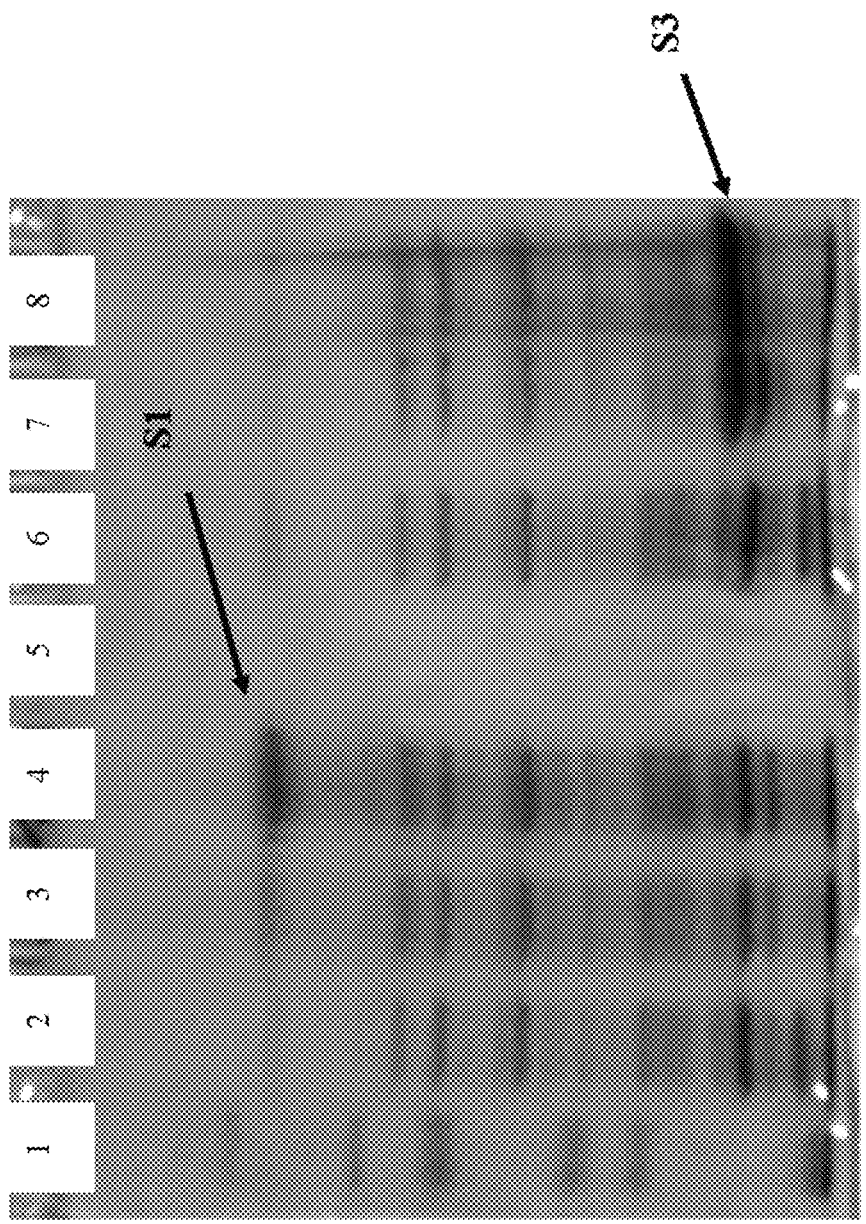

FIG. 4: 8% SDS-PAGE stained with Coomassie blue of recombinant glutenases.

Protein expression was induced with IPTG 0.2 μM at 22° C. overnight. S1 indicates the *E. coli* strain transformed with pET28b-endopep-140; S3 indicates the *E. coli* strain transformed with pET28b-endopep-40. Molecular weights of the marker used are indicated on the left.

From the left: lane 1=molecular weight marker; lane 2=S1 not induced; lane 3=S1 induced, 3 h harvest; lane 4=S1 induced, overnight (o.n.) harvest; lane 5=blank; lane 6=S3 not induced; lane 7=S3 induced, 3 h harvest; lane 8=S3 induced, o.n. harvest.

Figure 5A:
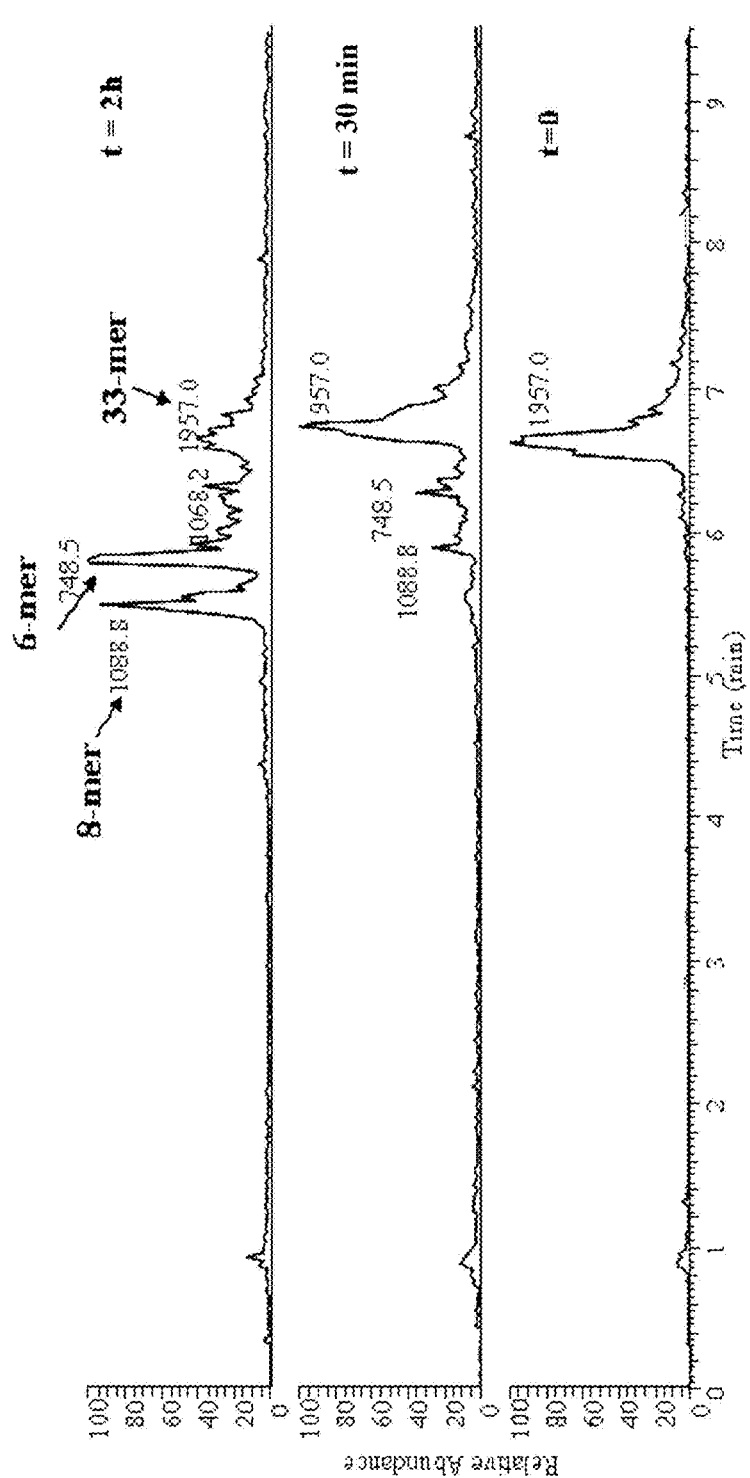

FIG. 5A: Breakdown of the 33-mer gliadin peptide by endopep-140.

The time course reaction products were separated by reversed phase HPLC. MS traces, ion counts m/z=300-2000.

Figure 5B:
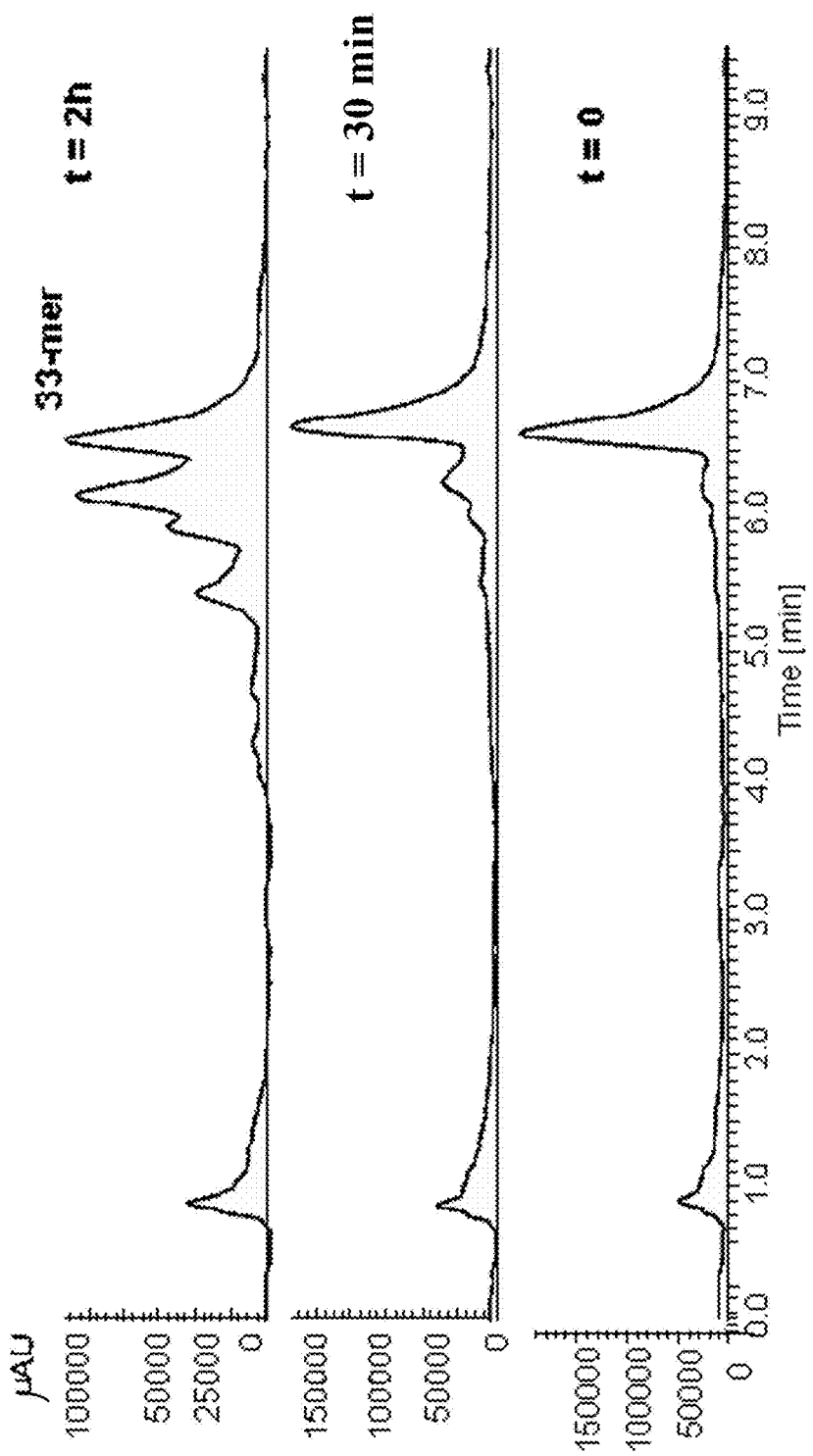

FIG. 5B: UV-profile 230 nm, μAU are absorbance micro units. The profile obtained at time 0, 30 min, 2 h are compared. Only one signal corresponding to the intact 33-mer peptide ([M-2H]=1957) was present at time 0. This signal decreased effectively with time. Several peaks appeared after 30 min incubation and their amount increased at time 2 h. All the molecular ions observed are reported in Table 2. The size of the most characteristic peak are highlighted in the figure.

Figure 6A:
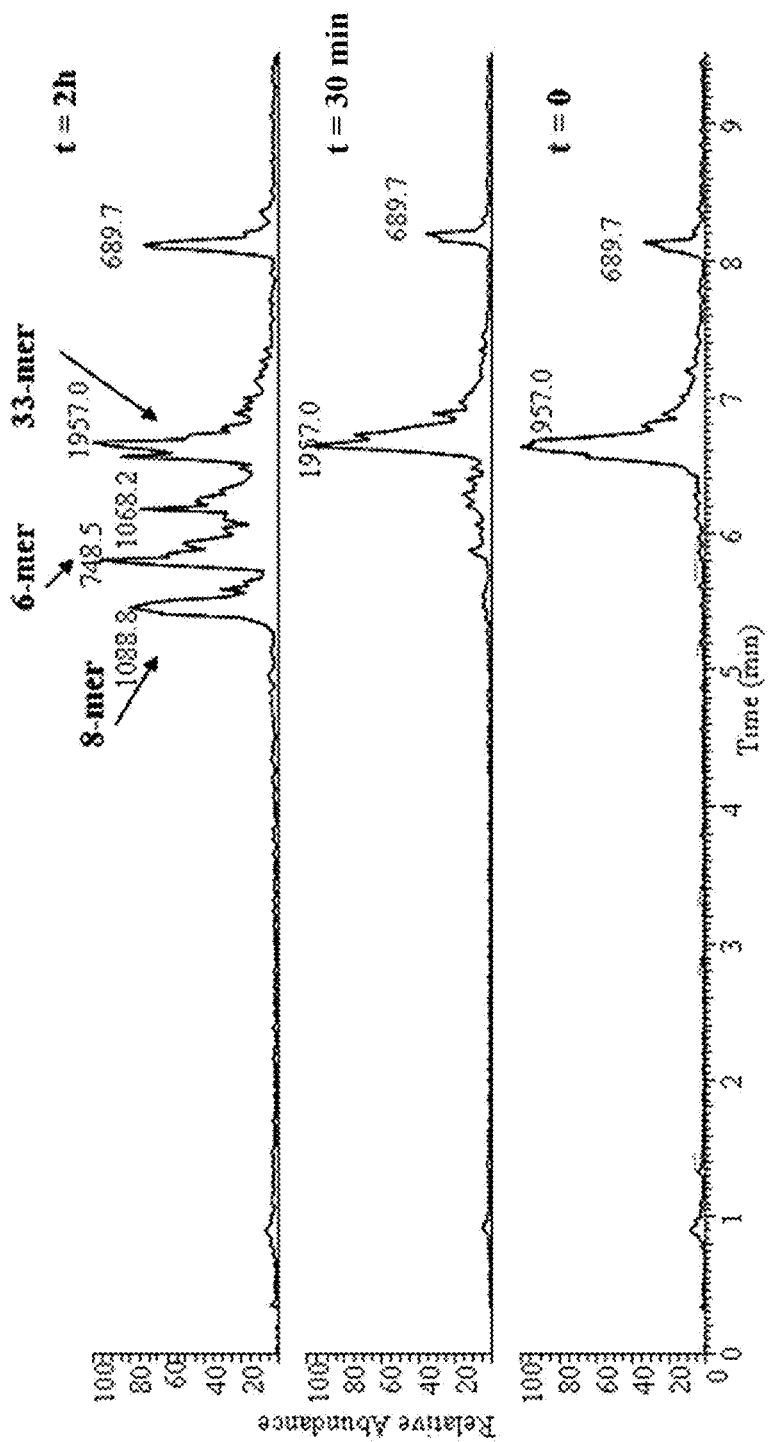

FIG. 6A: Breakdown of the 33-mer gliadin peptide by endopep-140 in the presence of pepsin (1 mg/ml).

The time course reaction products were separated by reversed phase HPLC. MS traces, ion counts m/z=300-2000.

Figure 6B:
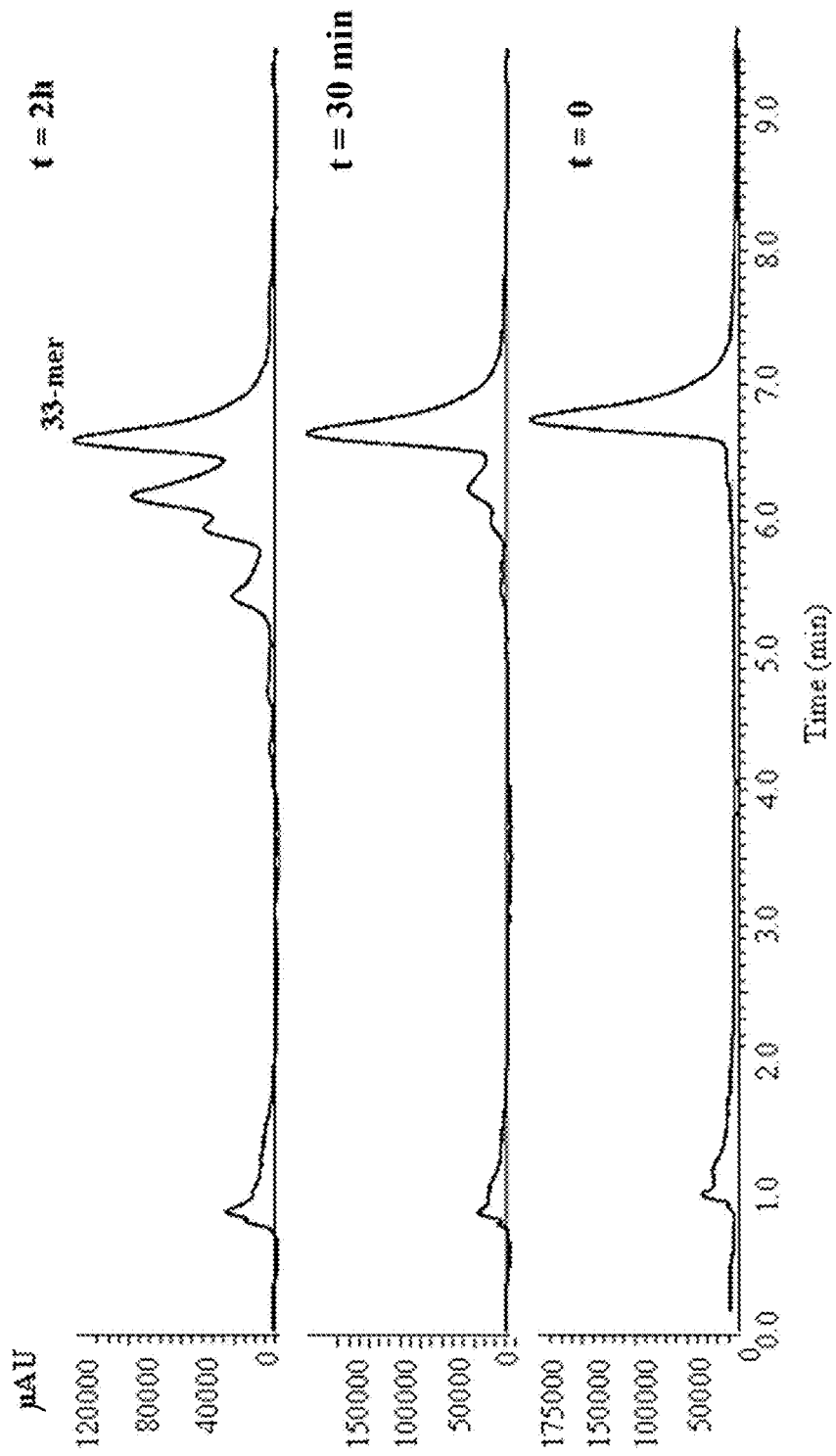

FIG. 6B: UV-profile 230 nm, μAU are absorbance micro units. The profile obtained at time 0, 30 min, 2 h are compared. While only one signal corresponding to the intact 33-mer peptide ([M-21H]=1957) was present at time 0, several peaks appeared after 30 min incubation and their amount increased at time 2 h. All the molecular ions observed are reported in Table 3. The size of the most characteristic peaks are highlighted in the figure. The signal at ([M-H]=1068) corresponds to a peptide of nine amminoacids present in the 33-mer sequence. The signal 689.7 is due to pepsin.

Figure 7A:
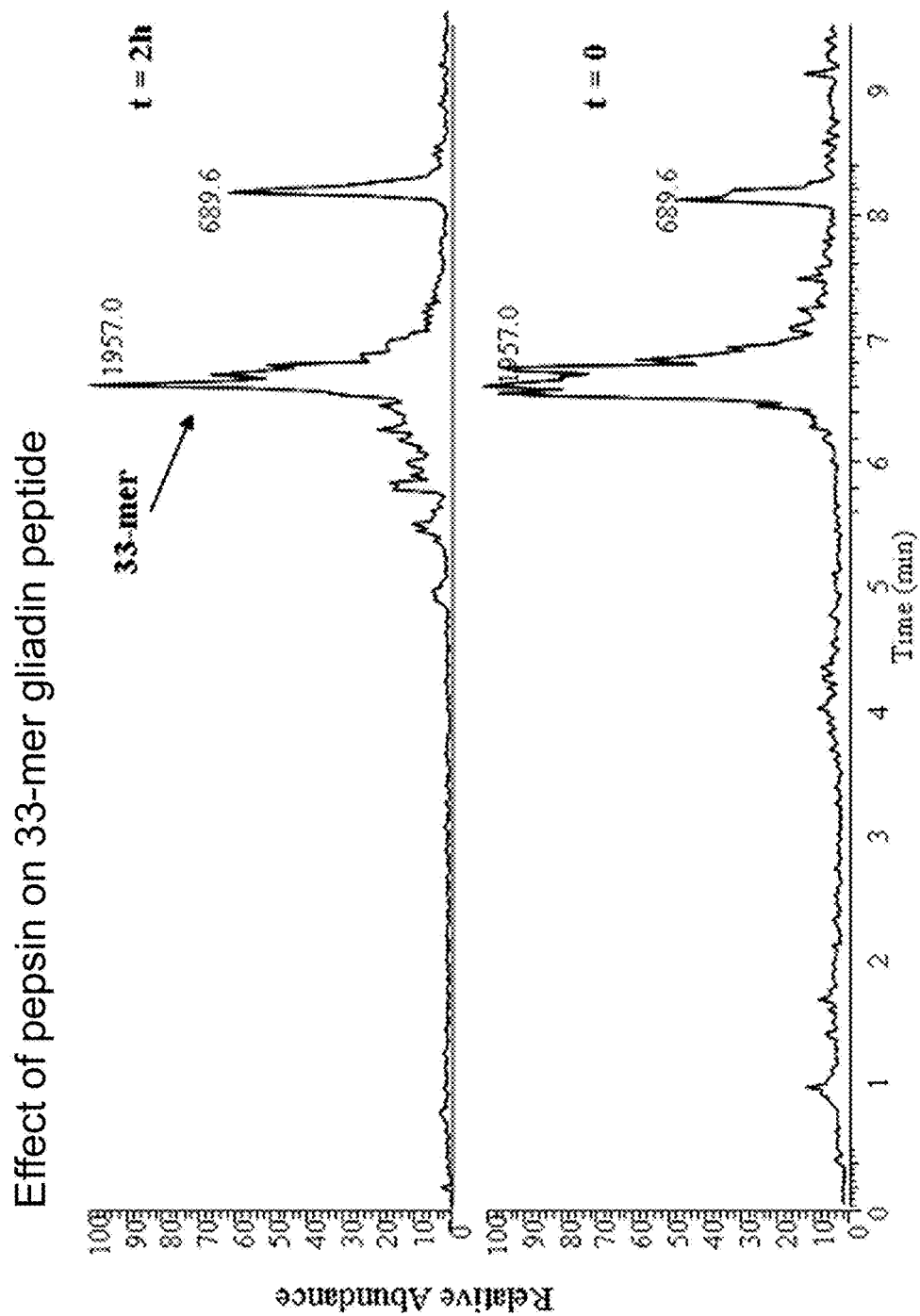

FIG. 7A: HPLC-MS analysis. 33-mer gliadin peptide was incubated with pepsin. MS traces.

Figure 7B:
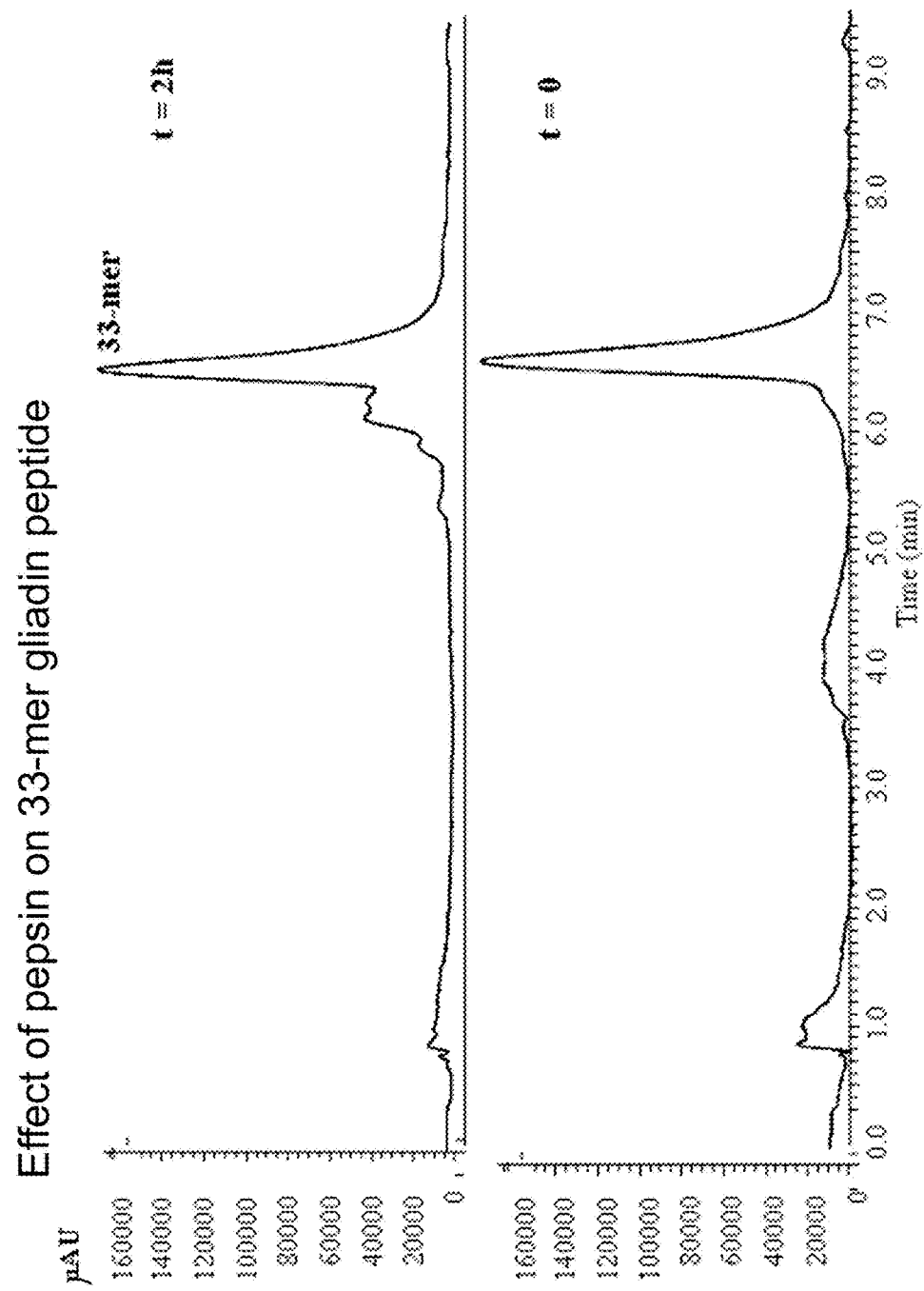

FIG. 7B: UV-profile 230 nm, μAU are absorbance micro units. The profile obtained at time 0 and 2 h are compared. Almost no degradation of 33-mer was observed.

Figure 8:
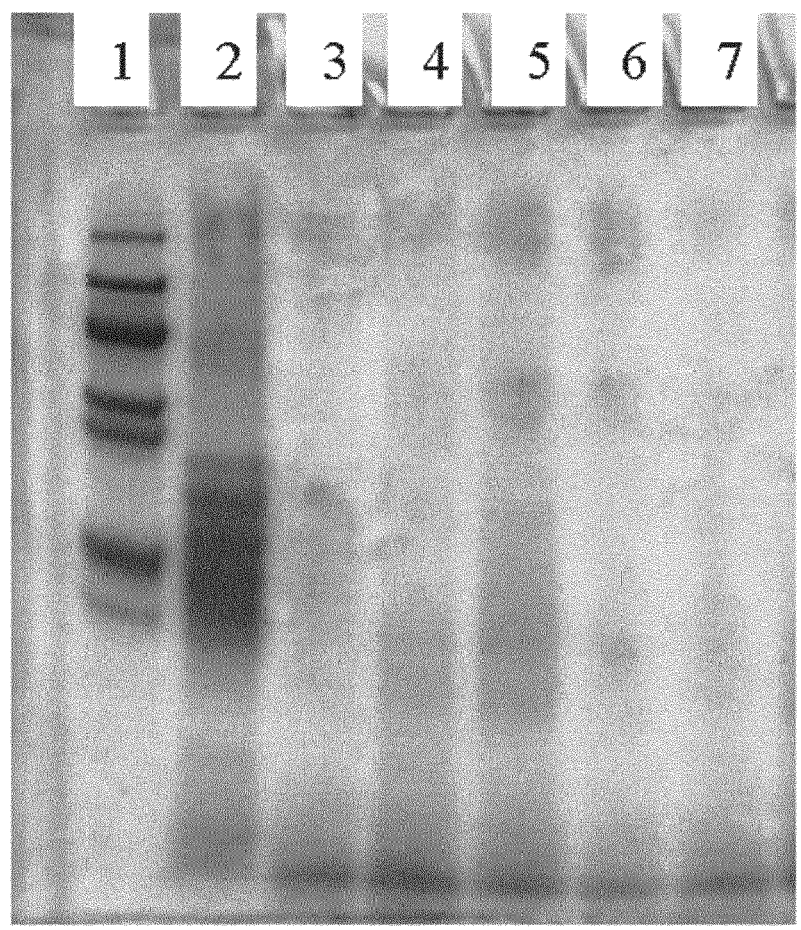

FIG. 8: Proteolysis of gliadin SDS-PAGE stained with Coomassie blue.

Gliadin digestion by the two different glutenases in presence or absence of pepsin. Gliadin was incubated 2 h at 37° C.

From the left: lane 1=Molecular weight marker; lane 2=gliadin; lane 3=gliadin+endopep-40 (<100 kDa); lane 4=gliadin+endopep-40 (<100 kDa)+pepsin; lane 5=reaction 3 stopped after 10 min incubation; lane 6=gliadin+endopep-140 (>100 kDa); lane 7=gliadin+endopep-140 (>100 kDa)+pepsin.

BRIEF DESCRIPTION OF TABLES

Table 1. Putative proteins purified from *Actinoallomurus* secretome.

Table 2. Peptides released by 33-mer digestion with endopep-140.

Table 3. Peptides released by 33-mer digestion with endopep-40.

DETAILED DESCRIPTION OF THE INVENTION

Actinomycetes are filamentous gram-positive bacteria, mainly known for their ability to produce secondary bioactive metabolites. Actinomycetes have been used as source of hydrolases, although only few, particularly the alkaliphilic ones, have so far been explored for their enzymatic potential (Endo A., Murakawa S., Shimizu H., Shiraishi Y. "Purification and properties of collagenase from a *Streptomyces* species" J. Biochem., 1987, 102, 163-70; Sakurai Y., Inoue H., Nishii W., Takahashi T., Iino Y., Yamamoto M., Takahashi K. "Purification and Characterization of a Major Collagenase from *Streptomyces parvulus*" Biosci. Biotechnol. Biochem., 2009, 73, 21-28; Mehta V. J., Thumar J. T., Singh S. P., "Production of alkaline protease from an alkaliphilic actinomycete" Bioresource Technology, 2006, 97, 1650-1654).

Moreover, the complete genome sequence of *Streptomyces coelicolor* A3(2) predicted the presence of 60 secreted putative proteases and peptidases among the 819 potential secreted proteins (Bentley S. D., Chater K. F., Cerdeño-Tárraga A. M., Challis G. L., Thomson N. R., James K. D., Harris D. E., Quail M. A., Kieser H., Harper D., Bateman A., Brown S., Chandra G., Chen C. W., Collins M., Cronin A., Fraser A., Goble A., Hidalgo J., Hornsby T., Howarth S., Huang C. H., Kieser T., Larke L., Murphy L., Oliver K. O'Neil S., Rabbinowitsch E., Rajandream M. A., Rutherford K., Rutter S., Seeger K., Saunders D., Sharp S., Squares R., Squares S., Taylor K., Warren T., Wietzorrek A., Woodward J., Barrell B. G., Parkhill J., Hopwood D. A., "Complete genome sequence of the model actinomycete *Streptomyces coelicolor* A3(2)" Nature, 2002, 417, 141-7) giving actinomycetes further value as potential source for new hydrolytic enzymes. Among the actinomycetes, acidophilic strains offer higher chances to produce enzymes with properties best fitting the requirements for being effective in CD, namely activity at acidic pH. Several new genera of acidophilic actinomycetes (i.e. *Catenulispora, Actinospica, Rugosimonospora, Streptacidiphilus*) as well as filamentous bacteria with acidophilic properties belonging to a previously unknown bacterial lineage (i.e. *Ktedonobacter*) have been described for the first time in recent years (Busti E., Cavaletti L., Monciardini P., Schumann P., Rohde M., Sosio M., Donadio S. "*Catenulispora acidiphila* gen. nov., sp. nov., a novel, mycelium-forming actinomycete, and proposal of Catenulisporaceae fam. nov." Int. J. Syst. Evol. Bacteriol., 2006, 56, 1741-1746; Cavaletti L., Monciardini P., Bamonte R., Schumann P., Rohde M., Sosio M., Donadio S. "New lineage of filamentous, spore-forming, gram-positive bacteria from soil" Appl. Env. Microbiol., 2006, 72, 4360-4369; Cavaletti L., Monciardini P., Schumann P., Rohde M., Bamonte R., Busti E., Sosio M., Donadio S. "*Actinospica acidiphila* gen. nov., sp. nov. and *Actinospica robiniae* gen. nov., sp. nov.; proposal for Actinospicaceae fam. nov. and Catenulisporinae subordo. nov. in the order *Actinomycetales*" Int. J. Syst. Evol. Bacteriol., 2006, 56, 1747-1753; Monciardini P., Cavaletti L., Ranghetti A., Schumann P., Rohde M., Bamonte R., Sosio M., Mezzelani A., Donadio S. "Novel members of the family Micromonosparaceae, *Rugosimonaspora acidiphila* gen. nov., sp. nov. and *Rugosimonospora africana* sp. nov" Int. J. Syst. Evol. Bacteriol., 2009, 59, 2752-2758; Kim S. B., Lonsdale J., Seong C. M., Goodfellow M. "*Streptacidiphilus* gen. nov., acidophilic actinomycetes with wall chemotype I and emendation of the family Streptomycetaceae (Waksman and Henrici (1943)$^{AL}$) emend. Rainey et al. 1997)" Antonie van Leewenhoek, 2003, 83, 107-116).

*Actinoallomurus*, like many other actinomycetes, can grow in a medium containing protein as the sole nitrogen and carbon source. This ability to grow in a protein medium depends on the synergic action of secreted endo- and exo-proteases since only aminoacids and short peptides can be assimilated via membrane transporters. *Actinoallomurus* strains have optimal growth at slightly acidic pH, thus suggesting that proteolytic enzymes may be expressed at this pH and may be able to digest complex proteins in acidic conditions. At Applicants' knowledge no other report describes the production of proteases acting at acidic pH from actinomycetes.

*Actinoallomurus* sp. DSM 24988 was isolated by Applicants from an Italian soil, stored in the Applicants' strain collection, and deposited on Jun. 24, 2011 with the DSMZ, Deutsche Sammlung von Mikroorganismen und Zellkulturen GmbH, Inhoffenstr.7b, D-38124 Braunschweig, Germany (now Leibniz-Institut DSMZ-Deutsche Sammlung von Mikroorganismen und Zellkulturen GmbH), under the provision of the Budapest Treaty. The strain was accorded accession number DSM 24988. *Actinoallomurus* sp. DSM 24988 grows on various standard solid media (Shirting E. B., Gottlieb D. "Methods of characterization of *Streptomyces* species" Int. J. Syst. Bacteriol., 1966, 16, 313-340) acidified at pH 5.5 with HCl, After 15 days of incubation at 28° C., the substrate mycelium is convolute, its colour is cream becoming violet with ageing and no aerial mycelium is produced on ISP2 agar. The colour of the aerial mycelium is white when formed on HSA5 (Busti et al., 2006). Abundant growth and production of convolute cream/brown vegetative mycelium was observed on ISP3 agar after 15 days of incubation. Slight production of brownish soluble pigments is present after 20 days of incubation. The strain can be grown at temperature between 21° C. and 35° C., optimal temperature being 28° C. on ISP2 and HSA5. *Actinoallomurus* sp. DSM 24988 is able to grow in the presence of NaCl up to 2.5% (w/v); at concentration of 1% (w/v) and higher the strain does not differentiate violet vegetative mycelium but only convolute cream substrate mycelium. The strain, plated on ISP2 agar adjusted to the desired pH values with HCl or NaOH, grows well at pH between 4.0 and 7.0, with an optimum pH5.5. Abundant convolute cream vegetative mycelium is observed when grown onto acidic ISP9 added with gluten. No aerial mycelium and soluble pigments are produced.

Proteomic investigation of the secreted *Actinoallomurus* proteins confirms that different sets of proteases active at neutral, basic or acidic pH are secreted and, in particular, several members of the S8/S53 peptidase family.

The glutenases of the invention belong to the MEROPS peptidase S8 [subfamilies S8A (subtilisin) and S8B (kexin)] and S53 (sedolisin) family (Rawlings N. D., Barrett A. J., Bateman A. "MEROPS: the peptidase database" Nucleic Acids Res., 2010, 38, D227-D233).

Gluten is a proteic component of wheat, barley, rye and related species, unique in its ability to provide elasticity and other desired characteristics to dough and many other food products. Gluten proteins are rich in glutamine (35%) and proline (15%) residues, a feature that is especially notable among gluten epitopes that are recognized by disease-specific T cells. The principal toxic components of wheat gluten are gliadins, a family of proline- and glutamine-rich proteins that contain several T-cell stimulatory epitopes. Their partial degradation in the gastrointestinal tract by pepsin, trypsin, chymotrypsin leads to the formation of several toxic peptides out of which peptides p31-49 and its derived p31-43 of the α1-gliadin fraction, and p56-88 (33-mer) of the α2-fraction are the best characterized. The 33-mer is a peptide fragment of 33 residues obtained also by in-vitro mimicking the physiological gastrointestinal enzymatic digestion (Shan et al., 2002), whose aminoacid sequence is LQLQP-FPQPQLPYPQPQLPYPQPQLPYPQPQPF (SEQ ID NO: 6). It is the strongest immunostimulator peptide as it carries multiple copies of three epitopes that are immunogenic in patients with celiac disease; it is thus responsible for a strong immunotoxic response (Qiao S. W., Bergseng E., Molberg O., Xia J., Fleckenstein B., Khosla C., Sollid M. L. "Antigen Presentation to Celiac Lesion-Derived T Cells of a 33-mer Gliadin Peptide Naturally Formed by Gastrointestinal Digestion" J. Immunol., 2004, 173, 1757-1762) and therefore it is used as a model for gluten detoxyfication. The 33-mer peptide is an excellent substrate for the enzyme transglutaminase 2 (TG2) that deamidates the gliadin peptides in the lamina propria, increasing their affinity to human leucocyte antigen (HLA) DQ2 or DQ8 molecules and thus enhancing the T cell-mediated mucosal immune response leading to the clinical consequences. Intestinal transport of intact 33-mer across the enterocyte layer may be due to an overexpression of transferrin receptor in CD and/or to an enhanced mucosal permeability. Anyway, the peptides can escape degradation by the acidic endosome-lysosomal pathway and can reach the serosal border unchanged. Degradation of the 33-mer gliadin peptide into peptides containing less than nine residues results in no gluten toxicity.

Since the gastrointestinal tract does not possess the enzymatic equipment to efficiently cleave the gluten-derived proline-rich peptides, driving in patients with celiac disease the abnormal immune intestinal response, the use of orally active proteases to degrade toxic gliadin peptides before they reach the mucosa can be considered as an alternative treatment to the diet.

Figure 1:
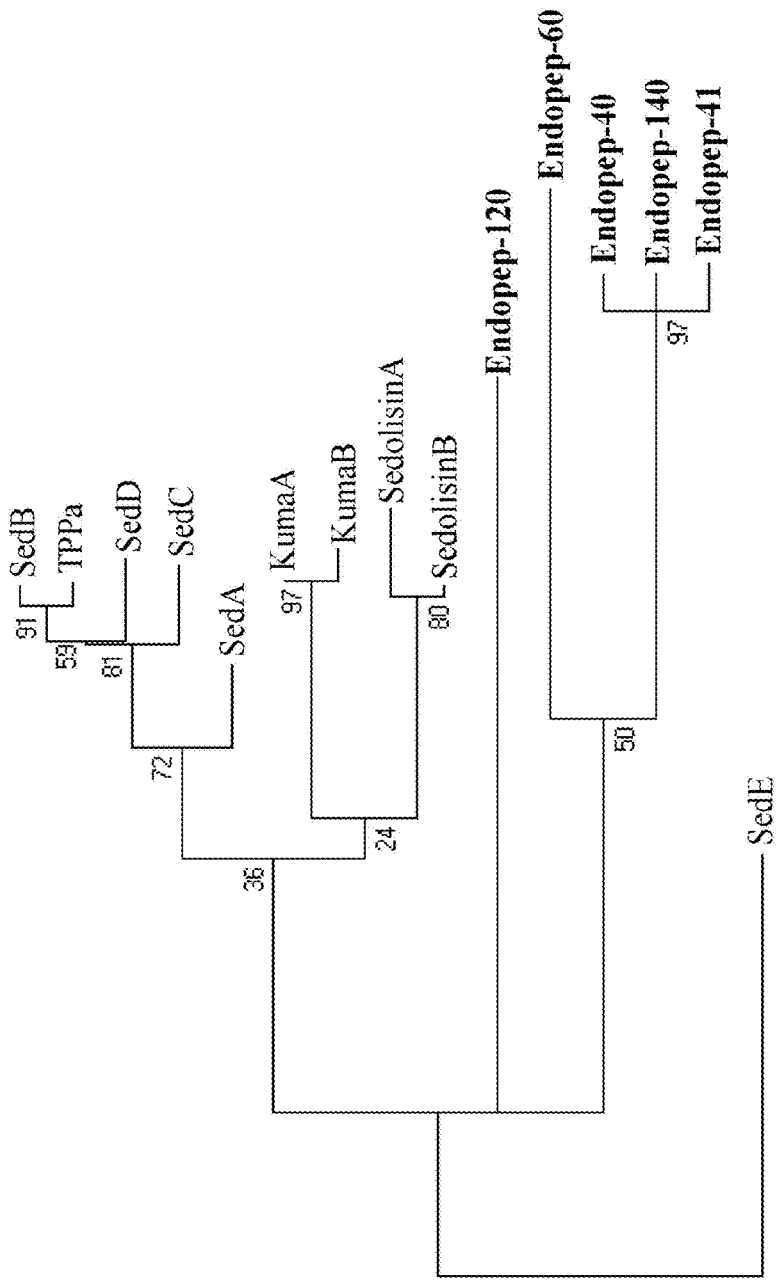
FIG. 1: Phylogenetic tree inferred from the sequences of glutenases of the invention and the sedolisin or kumamolisin proteases.

Applicants have identified a new sub-family of proteins which exhibits a proteolytic activity toward peptides, such as proline rich peptides, at acidic pH, which corresponds to the pH of the gastric fluid, and found that this enzyme composition is also able to degrade the 33-mer gliadin peptide. On the basis of structural properties, obtained by bioinformatic analysis, Applicants have shown that this new subfamily belong to peptidases S8/S53 (subtilisin kexin sedolisin) and can be grouped in a new subgroup different from the already known sedolisin or kumamolisin that belong to the S53 family (FIG. 1).

Applicants have developed a particular composition of these endopeptidases. This composition comprises at least one of the endoproteases of the peptidase S8/S53 (subtilisin kexin sedolisin) family produced by *Actinoallomurus* which digests full-length polypeptides and degrades a fragment of gliadin known to be resistant to protease action. So at least one endoprotease can be used for the treatment of celiac disease or any disease of the digestive process such as malabsorption. Moreover, as the enzyme is resistant to pepsin, a combination of these two proteolytic activities could result in more extensive degradation of polypeptides and proteins such as gliadin. Applicants have discovered that 33-mer is degraded to peptides of six aminoacids (Table 2 and 3). Although the enzymes of the invention are active alone, the addition to them of one or more peptidases that are acting on proline rich peptides such as prolyl-endoproteases and/or x-prolyl-dipeptidyl aminopeptidases and/or prolyl-aminopeptidases may result in a more rapid action.

The S8/S53 protein family of this invention alone or optionally in combination with other proteases can be useful in the food industry, such as, but not limited to, to degrade substrates for bitterness, treatment of meat, soap industry, or to degrade prions, viruses, and toxic or contaminant proteins into short peptides and/or free aminoacids.

Thus, the present invention provides an enzyme composition, comprising at least one S8/S53 endopeptidase active at pH between 3 and 8 (inclusive), selected from the group consisting of:

a) endopep-140 comprising SEQ ID NO: 1, a biologically active fragment thereof, a naturally occurring allelic variant thereof, or a sequence having at least 50%, 60%, 70%, 80%, 90%, or 95% of identity, b) endopep-40 comprising SEQ ID NO: 2, a biologically active fragment thereof, a naturally occurring allelic variant thereof, or a sequence having at least 50%, 60% 70%, 80%, 90%, or 95% of identity, c) endopep-120 comprising SEQ ID NO: 3, a biologically active fragment thereof, a naturally occurring allelic variant thereof, or a sequence having at least 50%, 60%, 70%, 80%, 90%, or 95% of identity, d) endopep-60 comprising SEQ ID NO: 4, a biologically active fragment thereof, a naturally occurring allelic variant thereof, or a sequence having at least 50%, 60%, 70%, 80%, 90%, or 95% of identity e) endopep-41 comprising SEQ ID NO: 5, a biologically active fragment thereof, a naturally occurring allelic variant thereof, or a sequence having at least 50%, 60%, 70%, 80%, 90%, or 95% of identity.

The term "peptidase(s) of the invention" "protease(s) of the invention", or "endopeptidase(s) of the invention" as used herein, identifies one or more of the endopeptidases defined above.

The present invention also includes an endopeptidase derived from any one of the sequences indicated above where any of the aminoacids may be changed from the corresponding residues shown in SEQ ID NOs: 1, 2, 3, 4 or 5 still maintaining its biological activity and physiological functions, or a biologically active fragment thereof. The object of this invention includes also any peptidase variant containing substitutions, deletions, side-chain modifications and/or insertions at certain positions within the aminoacid sequence of the native aminoacid sequence which preserves the biological activity and physiological function of said native aminoacid sequence. Examples of substitutions are well known to those skilled in the art and indicated, for example, in WO2011/077359.

In another aspect, the present invention is directed to isolated proteases of the invention, and biologically active fragments thereof (or derivatives, portions, analogs or homologs thereof). Biologically active fragment refers to regions of the proteases of the invention, which are necessary for specific protease activities.

In a further embodiment, the protease of the invention is a protease that comprises an aminoacid sequence having at least 50%, preferably at least 60%, more preferably at least 70%, even more preferably 80%, still more preferably 90% and most preferably 95% of identity to the aminoacid sequence comprising SEQ ID NOs: 1, 2, 3, 4 or 5 and retains the activity of the proteases comprising SEQ ID NOs: 1, 2, 3, 4 or 5.

The term "identity" and "homology" when referred to a nucleotide or aminoacid sequence are used interchangeably herein and refers to the degree to which two polynucleotide or polypeptide sequences are identical or homologous on a residue-by-residue basis over a particular region of comparison. The alignment and the percent identity or homology can be determined using any suitable software program known in the art, for example those described in Current Protocols in Molecular Biology (Ausubel F. M. et al., "Commercially Available Software", Current Protocols in Molecular Biology, 1987, Supplement 30, Section 7.7.18, Table 7.7.1). Preferred programs include the GCG Pileup program, FASTA (Pearson R. and Lipman D. J. "Improved Tools for Biological Sequence Analysis" Proc. Natl., Acad. Sci. USA, 1988, 85, 2444-2448), and BLAST (Altschul S. F., Gish W., Miller W., Myers E. W., Lipman D. J. "Basic local alignment search tool" J. Mol. Biol., 1990, 215, 403-410).

The invention also provides proteases of the invention operatively-fused to another polypeptide which are called chimeric or tagged proteins by those skilled in the art. The polypeptide can be fused to the N-terminus and/or C-terminus of the protease of the invention. Different tagged fusion proteins can be done by those skilled in the art and produced by standard recombinant DNA techniques or conventional techniques including automated DNA synthesizers. Such fusion proteins can facilitate the purification of the recombinant protease of the invention or their expression and secretion in host cells. These techniques are well known to those skilled in the art.

The Applicants have shown that large peptides such the 33-mer gliadin peptide can be degraded at acidic pH by the endopeptidases. The secreted endopep-140 acts by cleaving the polypeptide chain at several points generating different small peptides of six aminoacids (Table 2, FIG. 5). This endopeptidase shows a preference for sites having tyrosine or leucine or phenylalanine in position P1 and prolific in position P2 and P1'. Increasing the amount of endopeptidase and/or time of incubation leads to complete degradation of the 33-mer polypeptide. According to the molecular weights detected, it seems that glutamine residues are transformed to glutamic residues thus suggesting the involvement of an amidotransferase activity. The endopeptidases of the enzyme composition of the invention can operate in the presence of mammalian pepsin (Table 2, FIG. 6).

The same analyses were performed with endopep-40 and the results obtained, shown in Table 3, indicate that this glutenase behaves similarly.

The endopep-140 contains a structural domain with high homology to other endopeptidases of the invention. For example, BLAST alignment gives Identities=223/370 (60%), Positives=261/370 (71%) between endopep-140 and endopep-40 or Identities=227/431 (53%), Positives=273/431 (63%) between endopep-140 and endopep-41. Similar results are abtained by the BLAST alignment between endopep-40 and endopep-41, with Identities=230/419 (55%), Positives=278/419 (66%). Positives are aminoacid residues that are identical or very similar to each other in their physico-chemical features as determined with the BLOSUM62 matrix.

The endopeptidases of the enzyme composition of the invention can be produced by cultivation of a naturally occurring *Actinoallomurus* strain or a mutant thereof which is capable of producing at least one S8/S53 endopeptidase above defined or a host cell obtained by recombinant DNA techniques.

The term "recombinant", when used with reference to a cell, indicates that the cell replicates a heterologous nucleic acid, or expresses a peptide or protein encoded by a heterologous nucleic acid. Genes not found within the native (non-recombinant) form of the cell or found in the native form of the cell wherein the genes are modified and re-introduced into the cell by artificial means can be contained in recombinant cells.

The person skilled in the art will recognize that these cells can be unicellular or multicellular transgenic organisms.

The invention also includes methods based on cultivation of cells that contain a nucleic acid endogenous to the cell that has been modified without removing the nucleic acid from the cell; such modifications include those obtained by gene replacement, site-specific mutation, and related techniques, e.g. by treatment with mutagenic agents or with ionizing radiations.

The term "allelic variant" denotes any of two or more alternative forms of a gene occupying the same chromosomal locus. Allelic variation arises naturally through mutation, and may result in phenotypic polymrphism within populations. Gene mutations can be silent (no change in the encoded polypeptide) or may encode polypeptides having altered aminoacid sequence. The term allelic variant refers also to a protein encoded by an allelic variant of a gene.

Thus, the present invention provides a method for producing the enzyme composition of the invention which comprises:

A) cultivating a naturally occurring *Actinoallomurus* strain capable of producing at least one S8/S53 endopeptidase above defined and recovering the endopeptidase(s) from the cultivation batch; or B) cultivating an *Actinoallormurus* strain derived from a naturally occurring *Actinoallomurus* strain capable of producing at least one S8/S53 endopeptidase above defined by conventional mutation and/or selection techniques, which maintain the capability of producing at least one of the above defined endopeptidase(s) and recovering the endopeptidase(s) from the cultivation batch; or C) a recombinant DNA technique comprising the steps of:
1) introducing into a host cell a nucleic acid encoding for at least one endopeptidase of the S8/S53 subtilisin kexin sedolisin class selected from the group consisting of:
   a) endopep-140 comprising SEQ ID NO: 1, a biologically active fragment thereof, a naturally occurring allelic variant thereof, or a sequence having at least 50%, 60%. 70%, 80%, 90% or 95% of identity,
   b) endopep-40 comprising SEQ ID NO: 2, a biologically active fragment thereof, a naturally occurring allelic variant thereof, or a sequence having at least 50%, 60%. 70%; 80%, 90% or 95% of identity,
   c) endopep-120 comprising SEQ ID NO: 3, a biologically active fragment thereof, a naturally occurring allelic variant thereof, or a sequence having at least 50%, 60%. 70%, 80%, 90% or 95% of identity,
   d) endopep-60 comprising SEQ ID NO: 4, a biologically active fragment thereof, a naturally occurring allelic variant thereof, or a sequence having at least 50%, 60%. 70%, 80%, 90% or 95% of identity, and
   e) endopep-41 comprising SEQ ID NO: 5, a biologically active fragment thereof, a naturally occurring allelic variant thereof, or a sequence having at least 50%, 60%. 70%, 80%, 90% or 95% of identity,
2) cultivating the cell of step 1) in a culture medium under conditions suitable for producing the endopeptidase(s), and
3) recovering the endopeptidase s) from the cultivation batch.

One or more endopeptidases of the invention may be produced in performing one method as above defined. When single endopeptidases are separately produced performing the method defined above, this invention includes optionally the step of combining two or more of the obtained endopeptidases to provide an enzyme composition containing a mixture of the said endopeptidases. Said endopeptidases may be obtained as isolated endopeptidases. With the term "isolated endopeptidase", as used herein, a purified form of the endopeptidase is intended which is substantially free of other proteins or cellular material from the cell from which the endopeptidase is derived.

All DNA/RNA nucleic acid terms also referred to their related manipulation techniques herein used are well known to those expert in the molecular biology art and so far these terms are used in all their wide and common meaning as reported in Maniatis T., Fritsch E. F., Sambrook J. "Molecular cloning: a laboratory manual" Cold Spring Harbor, N.Y., 1982 or Ausubel F. M. "Current Protocols in Molecular Biology" John Wiley & Sons, New York, N.Y., 1993 or Sambrook et al., "Molecular Cloning: a Laboratory Manual $2^{nd}$ Ed.", Cold Spring Harbor Laboratory Press, Cold Spring Harbor, N.Y., 1989.

The nucleic acids encoding the endopeptidases of the enzyme composition of the invention are a further object of the invention which includes the nucleic acids whose sequences are provided herein and defined as SEQ NOs: 7, 8, 9, 10 or 11 or fragments thereof. The invention also includes mutant or variant nucleic acids or portion of these nucleic acids.

Accordingly, the nucleic acids of this invention include a polynucleotide sequence shown in SEQ ID NOs: 7, 8, 9, 10 or 11 or a sequence having at least 50%, preferably 60%, more preferably at least 70%, even more preferably 80%, still more preferably 90% and most preferably at least 95% of identity to the nucleic acid sequence comprising SEQ NOs: 7, 8, 9, 10 or 11 and is encoding an aminoacid sequence which is still maintaining the biological activity and physiological function of said aminoacid sequence.

Sequences characterized by identities at the nucleotide level are indicated herein also as "homologous nucleic acid sequences" or variations thereof. Homologous nucleotide sequences encode those sequences coding for isoforms of proteases of the invention. Isoforms can be expressed in the same organism as a result of, for example, alternative splicing of RNA. Alternatively, isoforms can be encoded by different genes.

Homologous nucleotide sequences also include, but are not limited to, naturally occurring allelic variations and mutations of the nucleotide sequences set forth herein. Homologous nucleic acid sequences include those nucleic acid sequences that encode conservative aminoacid substitutions in SEQ ID NOs: 1, 2, 3, 4 or 5.

In the invention, homologous nucleotide sequences can include nucleotide sequences encoding a protease of the invention of other species belonging to Actinoallomurus as well as of genera other than Actinoallomurus, such as for example Catenulispora, Actinospica, Ktedonobacter, Streptomyces, Streptacidiphilus, Micromonospora, Rugosimonospora.

Applicants determined by BLAST analysis that Catenulispora, Ktedonobacter, Streptomyces genomes contain genes that encode for proteins having more than 50% homology with the corresponding protease of the invention; for example, the putative proteins with accession numbers ACU72534 and ACU72320 of Catenulispora acidiphila have Identities=261/400 (65%), Positives=295/400 (74%) with endopep-40 SEQ ID NO: 2 and Identities=705/1342 (53%), Positives=878/1342 (65%) with endopep-140 SEQ ID NO: 1 respectively, or the putative protein with accession number EFH81837 of Ktedonobacter racemifer has Identities=244/402 (61%), Positives=299/402 (74%) with endopep-40 SEQ ID NO: 2, or Streptomyces sp. e14 protein sequence with accession number EFF91270 has Identities=230/371 (62%), Positives=274/371 (74%) with endopep-40 SEQ ID NO: 2, as well. Homologous endopeptidase encoding genes may be present in strains belonging to genera phylogenetically related to the above mentioned whose genomic sequences are not available by public databases.

A "biologically-active fragment" of the endoprotease of the invention can be prepared by isolating a nucleic acid fragment of SEQ ID NOs: 7, 8, 9, 10 or 11, that encodes an endoprotease with the same biological activity of the endoproteases of the invention, expressing the encoded portion of endoprotease (for example, by recombinant expression in vitro) and assessing the activity of the encoded fragment of endoprotease. The invention further encompasses nucleic acid molecules that differ from the nucleic acid sequences shown in SEQ ID NOs: 7, 8, 9, 10 or 11 due to degeneracy of the genetic code and thus encode the same proteases that are encoded by the nucleic acid sequences shown in SEQ ID NOs: 7, 8, 9, 10 or 11.

The techniques for gene manipulation and protein expression are known to those skilled in the art and can be found also in Kriegler M. "Gene Transfer and Expression: A Laboratory Manual" Stockton Press, N.Y., 1990.

Applicants indicate with the term "biological activity" or "functional activity" the natural or normal function of the proteases of the invention, for example, the ability to degrade other proteins. Aminoacid residues that are conserved among the proteases of the invention are predicted to be particularly non-amenable to alteration. Aminoacids for which conservative substitutions can be made are well known within the art. As all the persons skilled in the art recognize, each codon in a nucleic acid (apart from AUG, which is ordinarily the only codon for methionine) can be modified to yield a functionally identical molecule by standard techniques. Furthermore, individual substitutions, deletions or additions which alter, add or delete a single aminoacid or a small percentage of aminoacids (typically less than 5%, more typically less than 1%) in an encoded sequence are "conservative mutations" where the alterations result in the substitution of an aminoacid with a chemically similar aminoacid.

Another aspect of the invention pertains to nucleic acid molecules encoding the proteases of the invention that contain changes in aminoacid residues that are not essential for activity. Such proteases of the invention differ in aminoacid sequence from SEQ ID NOs: 1, 2, 3, 4 or 5, yet retain biological activity. In one embodiment, the isolated nucleic acid molecule comprises a nucleotide sequence encoding a protease, wherein the protease comprises an aminoacid sequence with at least about 50% identity to the aminoacid sequences of SEQ NOs: 1, 2, 3, 4 or 5.

The term "isolated nucleic acid" or "isolated polynucleotide sequence", as used herein, identifies a nucleic acid molecule which is separated from other nucleic acid molecules that are present in the cell from which the nucleic acid is derived and is substantially free of other cellular material or culture medium material when said nucleic acid molecule is obtained from a naturally occurring microorganisms, a microorganism derived therefrom, or microorganisms obtained by recombinant techniques.

An isolated nucleic acid molecule encoding an endoprotease of the invention homologous to the protein of SEQ NOs: 1, 2, 3, 4 or 5, can be created by introducing one or more nucleotide substitutions, additions or deletions into the nucleic acid sequence of SEQ ID NOs: 7, 8, 9, 10 or 11, such that one or more aminoacid substitutions, additions or deletions are introduced into the encoded protease. Mutations can be introduced into SEQ ID NOs: 7, 8, 9, 10 or 11, by standard techniques, such as site-directed mutagenesis, PCR-mediated mutagenesis and DNA shuffling. Alternatively, mutations can be introduced randomly along all or part of a coding sequence of the protease of the invention, such as by saturation mutagenesis, and the resultant mutants can be screened for biological activity of the protease of the invention to identify mutants that retain activity.

The glutenase enzyme composition according to the present invention may also be used in immobilized form and used, for example, for the treatment of liquid food products. The enzyme composition of the invention can also be used in the fruit and brewing industry for equipment cleaning and maintenance. For example, a gluten containing liquid food product is allowed to flow along a matrix permeable for gluten in which the enzyme composition of the invention is embedded. The gluten is extracted from the food product and digested by the action of the enzymes. The enzyme composition of the invention can also contribute to the available energy of the food. For example a partially or indigestible proline-comprising protein is fully or partially degraded by the enzyme composition of the invention, resulting in availability of more digestible food for the human or animal. So, the growth rate and/or food conversion ratio (i.e. the weight of ingested food relative to weight gain) of the human or animal is improved.

Methods of Production of the Endopeptidases and their Characterization

The present invention also relates to methods for producing the enzymes of the present invention comprising cultivating (a) a strain, which in its wild-type form, or (b) a form derived therefrom by common mutation techniques, e.g., by treatment with mutagenic agents or with ionizing radiations, or (c) a host cell which is capable of producing the polypeptide of the invention, and recovering said polypeptide from the cultivation batch. In the production methods of the present invention, the media for cell cultivation are differently selected among those known in the art for protein production according to cultivation of wild type strains, strains derived therefrom, or recombinant host cells. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). For example, medium containing soya are more apt to allow production of enzymes of the invention by wild type microorganisms.

The cells may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. If the polypeptide is secreted into the nutrient medium, the polypeptide can be recovered directly from the medium. If the polypeptide is not secreted, it can be recovered from cell lysates. Several proteolytic activities are produced and cultivation is suspended when the production of endopeptidase has reached a maximum. After the completion of cultivation, the culture medium is filtered off to separate microbial bodies, and the filtrate is processed in the usual way for the collection of endopeptidase by several procedures in combination, such as ultrafiltration, concentration under reduced pressure, salting out, precipitation by organic solvent, dialysis, gel filtration, adsorption chromatography, ion-exchange chromatography, electro-focusing, and freeze-drying. Adequate procedures should be selected taking into account the desired physical and chemical properties of endopeptidases.

A representative example of production of endopeptidases of this invention by cultivating a wild-type *Actinoallomurus* strain is provided in Example 1 hereinafter. The endopeptidase(s) of the invention may be purified to the desired degree of purity which may depend on the intended use and on the specific activity of endopeptidase(s).

Heterologous Expression in Host Cells

Recombinant cells and microorganisms can be used to produce the endopeptidases of the present invention. The host cell may be any of the host cells familiar to the person skilled in the art, including prokaryotic cells, eukaryotic cells, mammalian cells, insect cells, fungal cells, yeast cells and/or plant cells. The selection of an appropriate host is within the abilities of the person skilled in the art.

Useful microorganisms are bacterial cells such as gram positive bacteria including, but not limited to, a *Bacillus* cell (e.g. *Bacillus subtilis, Bacillus cereus*) or a *Streptomyces* cell, or cells of lactic acid bacteria, or grain negative bacteria such as *E. coli* and *Pseudomonas*. Preferred producing cells include those from organisms known to be generally regarded as safe, such as the prokariots *Lactobacillus, Pyrococcus, Bacillus, Streptomyces*, and the eukariot *Aspergillus*. More preferred cells include those that are already used in the preparation of foodstuffs, such as *Lactobacillus* spp. and/or *Aspergillus oryzae*.

Extracellular production of the enzymes may be obtained from microorganisms such as *Aspergillus oryzae, Lactobacillus casei, Kluyveromyces lactis* or *Streptomyces lividans*.

The introduction of a vector into a bacterial host cell may, for instance, be done by protoplast transformation (e.g., Chang S., Cohen S. N. "High frequency transformation of *Bacillus subtilis* protoplasts by plasmid DNA" Mol. Gen. Genet., 1979, 168, 111-115), using competent cells (e.g., Dubnau D., Davidoff-Abelson R. "Fate of transforming DNA following uptake by competent *Bacillus subtilis*. I. Formation and properties of the donor-recipient complex" J. Mol. Biol., 1971, 56, 209-221), electroporation (e.g., Shigekawa, K., Dower W. J. "Electroporation of eukaryotes and prokaryotes: a general approach to the introduction of macromolecules into cells" Biotechniques, 1988, 6, 742-751) or conjugation (e.g., Koehler T. M., Thome C. B. "*Bacillus subtilis* (natto) plasmid pLS20 mediates interspecies plasmid transfer" J. Bacteriol., 1987, 169, 5771-5278).

Useful multicellular organisms to be used as host cells are, for example, plants, plant parts, seeds or plant cells. Preferred producing multicellular organisms are, for example, transgenic food crops, such as grains, or vegetables, such as tomato, that contain the nucleic acids encoding the proteases of the invention.

A representative example of production of endopeptidases of this invention in recombinant host cells is given in Example 2 hereinafter.

Pharmaceutical Formulations

The endopeptidase agents of the present invention may be administered alone or incorporated into a variety of formulations. A pharmaceutical composition of the invention is formulated to be compatible with its intended route of administration, which is preferably the oral administration. For example, since some of the endopeptidases of the enzyme composition of the invention is secreted, a crude preparation obtained from cell culture medium of *Actinoal-*

*lomurus* or other useful unicellular recombinant microorganisms such as gram positive bacteria including, but not limited to, a *Bacillus* cell, a *Streptomyces* cell, lactic acid bacteria cells, gram negative bacteria such as *E. coli*, can be administered orally. lactic acid bacteria include, but are not limited to, species of the genera *Lactococcus, Lactobacillus, Leuconostoc, Streptococcus, Pediococcus*, and *Enterococcus*. Alternatively, the enzyme composition of the invention can be administered orally after purification.

Such formulations can be prepared with the appropriate ingredients to generate a preparation in liquid form, for example in the form of a solution, emulsion, or in solid form, such as tablets, capsules, or semisolid. The formulation of the enzyme composition can be administered in a variety of ways including those particularly suitable for admixing with foodstuff. The enzyme components can be active prior to or during ingestion, and may be treated, for example, by a suitable encapsulation, to control the timing of activity.

To prepare an appropriate pharmaceutical composition of the endopeptidases of the present invention any method for the stabilization of chemical or biological material known in the art, comprising those based on irradiation or temperature modulation or their combinations, can be used.

For treating celiac disease, the pharmaceutical compositions employed are preferably formulated so as to release their activity in the gastric fluid. This type of formulations will provide optimum activity in the right place, for example the release of the endoproteases of the invention in the stomach.

Alternatively a microorganism, such as a bacterial or yeast culture, able of producing the active agents can be administered to a patient. Such a culture may be admixed with food preparations or formulated, for example, as an enteric capsule.

The present invention further provides a food supplement comprising the enzyme composition of the present invention. The term "food supplement" in the context of the present invention is interchangeable with the terms food additive, a dietary supplement and nutritional supplement.

The food supplement of the invention can be formulated, prepared, supplied and dispensed as described in other prior documents regarding the field of this invention (WO2011/077359, WO 2003/068170, WO2005/107786) that provide methods for treating and/or preventing a syndrome associated with a human disease, said disease being selected from the group comprising celiac disease, dermatitis herpetiformis, digestive tract bad absorption, an allergic reaction, an enzyme deficiency, a fungal infection. Crohn disease, mycoses and sprue.

As an example, the food supplement of the invention may be a granulated enzyme coated or uncoated product which may readily be mixed with food components, alternatively, food supplements of the invention can form a component of a pre-mix. Alternatively, the food supplements of the invention may be a stabilized liquid, an aqueous or oil-based slurry. The enzyme composition of the invention can be supplied by expressing the enzymes directly in transgenic food crops (as, e.g., transgenic plants, seeds and the like), such as grains, cereals, corn, soy bean, rape seed, lupin.

The pharmaceutical composition or the food supplement of the invention can be provided prior to meals, immediately before meals, with meals or immediately after meals, so that the endoproteases of the enzyme composition of this invention are released or activated in the upper gastrointestinal lumen where the endoproteases can complement gastric and pancreatic enzymes to detoxify ingested gluten and prevent harmful peptides to pass the enterocytes layer.

The enzyme composition of this invention has numerous applications in food processing industry, in particular they can be used in the manufacture of food supplements as described in the above mentioned prior documents.

From this description it results evident that a further object of this invention consists in providing a method for degrading gluten oligopeptides which are resistant to cleavage by gastric and pancreatic enzymes and whose presence in the internal lumen results in toxic effects which comprises contacting said gluten oligopeptides with an enzyme composition or at least one isolated endopeptidase of this invention.

In particular, one aspect of said method consists in the treatment or prevention of celiac sprue, dermatitis herpetiformis and/or any other disorder associated with gluten intolerance which comprises administering to a patient in need thereof an effective amount of an enzyme composition or of at least one isolated endopeptidase of this invention, preferably, incorporated into a pharmaceutical formulation, food supplement, drink or beverage.

EXAMPLES

Example 1: *Actinoallomurus* sp. DSM 24988
Endopeptidases Identification and Characterization 1.1 Strain Cultivation and Protein Production The *Actinoallomurus* strain used according to this invention derives from the Applicants strain collection.

*Actinoallomurus* sp. DSM 24988 was maintained on ISP2 agar medium (Shirling and Gottlieb, 1966) acidified at pH 5.5 with HCl. The microbial content of one plate was scraped and inoculated into one 50 ml Erlemneyer flask containing 15 ml of medium AF5 which is composed of: (g/l) dextrose 20, yeast extract 2, soybean meal 8, NaCl 1 and MES 10. Medium was prepared in distilled water and pH adjusted to 5.5 prior to sterilization at 121° C. for 20 min. The inoculated flask was grown at 28° C., on a rotary shaker operating at 200 rpm. After 5-6 days incubation, 5% of culture was inoculated into a second series of 500 ml Erlenmeyer flasks containing 100 ml of the same fermentation medium. Protein production was performed in flasks incubated for 15 days at 28° C. on a rotary shaker operating at 200 rpm. The production of the protein was monitored by bioassay as described below.

Several proteolytic activities are produced and cultivation is suspended when the production of endopeptidases, followed by the assays described below, has reached a maximum. The fermentation was harvested after 15 days and the broth was centrifuged at 4000 rpm for 15 minutes. The culture medium was filtered off to separate microbial bodies, and the filtrate was processed. Adequate procedures were selected taking into account the desired physical and chemical properties of endopeptidases.

1.2 Proteolytic Activities Determination

Enzyme activities were measured at different pHs in acetate buffer (ammonium acetate-AMAC, 50 mM final concentration, pH 4.0 to 8.0; acetic acid 20 mM, pH3.0) at 37° C. in a total volume of 0.2 ml.

The enzymatic activity of endopeptidase was determined by measuring the hydrolysis of Succinyl-Ala-Ala-Pro-Phe-AMC (Amino-Methyl-Coumarine) as substrate (Bachem A G, Hauptstrasse 144, 4416 Bubendorf, Switzerland).

Substrate stock solutions were prepared at 10 mM concentration and stored at −20° C. The substrate was prepared from 10-20 µl of 60% methanol solution containing 2 mM Succinyl-Ala-Ala-Pro-Phe-AMC and 50-150 µl acetate buffer solution. The reaction mixture contained a concentration of 0.2 mM substrate and the enzyme preparation (between 10-40 µl or 1.0 µg per assay) in 200 µl acetate buffer at different pH values.

To the substrate, which had previously been heated to 37° C. for 10 minutes, 10-40 µl of the enzyme solution were added, and the reaction was performed at 37° C. up to 2 hours. The released AMC was measured with a Fusion micro-plate reader (Perkin Elmer Italia SpA, Monza, Italia) at an excitation wavelength of 360 nm and an emission wavelength of 460 nm. As control, the substrate was incubated without enzyme.

The enzymatic activity to release 1 mmol of AMC in 1 minute is defined as 1 Unit.

1.3 Endopeptidase Purification

The mycelium was separated from culture medium by paper filtration (Miracloth from Calbiochem, USA). Thereafter, 200 ml of supernatant were centrifuged for 10 minutes at 5000 rpm to remove debris, then the supernatant was further centrifuged at 10000 rpm for 20 min at 4° C. to remove the unsoluble fraction. Proteins were precipitated from surnatant by ethanol (1:4 v/v) or ammonium sulphate 20-75% saturation. Pellet was resuspended and dialyzed, at occurrence concentrated using a Centricon Plus-70 with a 5 kDa cut-off (Millipore, Bedford, Mass., USA). The presence of proteases able to hydrolyze Succinyl-Ala-Ala-Pro-Phe-AMC was highlighted when tested at pH5. Aliquots of the protein suspension after dialysis were boiled to be submitted to MS-shotgun analysis. The boiling procedure is necessary in order to avoid auto digestion. At least 5 proteins belonging to the S8/S53 family protease were detected.

Resuspended proteins were chromatographed on ionic exchange resin Amberlite IRA900 (Alfa Aesar GmbH, Karlsruhe, 76185 Germany) or DE-52 cellulose (Whatman Inter. Ltd, Maidstone England) or other matrix; the obtained fractions were tested for Succinyl-Ala-Ala-Pro-Phe-AMC hydrolysis and the pooled active fractions subjected to ID-SDS-PAGE and zymographic analysis.

Proteins were further fractionated by size exclusion filtration on molecular weight cut-off 300 kDa, 100 kDa, 50 kDa, 30 kDa, 10 kDa (Nanosep Pall, Mich. USA, Vivaspin Sartorius GmbH 37070 Goettingen, Germany). Their activity was tested as described. Active fractions with different molecular weight were obtained. Aliquots of these fractions were boiled and analyzed by MS-shotgun.

Proteins were separated by electrophoresis on a homogeneous 10% or disc-gel 4-15% or any-kd polyacrylamide gel (Bio-Rad, Hercules, 9640, Calif., USA) followed by staining with Coomassie Brilliant blue R-250 (Bio-Rad) or silver (SIGMA-Aldrich, USA) or by enzyme activity staining (zymography) performed by incubating the gel at 37° C. with 50-10 µM fluorescent substrate Succinyl-Ala-Ala-Pro-Phe-AMC at the desired pH.

Two endopeptidases belonging to the S8/S53 family were purified until the electrophoretic analysis showed the presence of a single band as detected both by silver staining and zymography.

The first endopeptidase was obtained after molecular weight filtration: it was retained on a cut-off of >100 kDa. The MS-shot gun analysis of the corresponding boiled aliquot revealed the presence of endopep-140, SEQ ID NO: 1 (Table 1A), with a molecular weight of 142449.4 and a theoretical pI of 5.18; traces of two other proteins were detected. This protein fraction resulted active in the pH range from 4 to 8 with a pH optimum of 5 (FIG. 2). When tested at pH3 the enzyme shows 95% of its activity at pH 5 after 30 minutes of incubation at 37° C. (FIG. 3). This protein fraction resulted more efficient in 33-mer digestion than in the hydrolysis of the Succinyl-Ala-Ala-Pro-Phe-AMC as shown in example 3.

The second glutenase, indicated as endopep-40, SEQ ID NO: 2, was contained in the <100 kDa cut-off protein fraction (Table 1B) with a molecular weight of 39908.4 and a theoretical pI of 5.94. This protein resulted active in the pH range from 4 to 6 with a pH optimum of 5. When tested at pH 3 the enzyme shows 85% of its activity at pH 5 after 30 minutes of incubation at 37° C. (FIG. 3). The fluorescent band highlighted by zymography shows a molecular weight of about 40 kDa. Either active protein eluted from gel band or correspondent molecular size cut-off retentate were characterized for enzymatic activity. The MS-shot gun analysis revealed the presence of other proteins; the signals indicating the presence of endopep-140 sequences may be due to smaller polypeptides (<100 kDa) formed by its degradation.

The other three endopeptidases (indicated as endopep-120, SEQ ID NO: 3, endopep-60, SEQ ID NO: 4, endopep-41, SEQ ID NO: 5) were not purified to homogeneity. Their presence was detected by MS-shotgun in the secretome and in the active fractions of the first purification steps. The MS-shotgun analysis allowed the identification of their aminoacid sequence, here reported. Applicants named the proteins according to their inferred molecular weight. So, endopep-120 has a molecular weight of 112012.8 and a theoretical pI of 6.75, endopep-60 has a molecular weight of 59646.0 and a theoretical pI of 6.02, endopep-41 has a molecular weight of 41646.1 and a theoretical pI of 5.22.

1.4 Protein MS Analysis: Shotgun MS Experiments

Today, proteomic methodologies are of primary importance for discovery-driven biomarker or protein characterization studies.

The classic proteomic approach is based on two-dimensional gel electrophoresis (2DG), where the protein spots of interest are isolated and identified by mass-spectrometry (MS). The 2DG approach has a relatively high resolution, which is limited however by the difficulty in detecting certain classes of proteins. These include membrane proteins due to their low solubility in gel electrophoresis buffer, proteins with an either low (<10 kDa) or high (≥200 kDa) molecular weight, as well as those with an extreme isoelectric point (pI<4 or >9). An additional limitation of this approach resides in the difficulty in analysis of less represented proteins and in the fact that it is tedious and time-consuming.

These problems are solved using a new proteomic methodology based on two-dimensional capillary chromatography coupled to tandem mass spectrometry (2DC-MS/MS), also named MudPIT (Multidimensional Protein Identification Technology) (Washburn, M. P., Wolters D., Yates J. R. 3rd "Large-scale analysis of the yeast proteome by multidimensional protein identification technology" Nat. Biotechnol., 2001, 19, 242-7). It involves the generation of peptides from enzymatic digestion of a complex protein mixture, their separation by means of two micro-HPLC columns and direct analysis of eluted peaks by MS/MS. 2DC-MS/MS combines ion exchange with reversed-phase separation of peptide mixtures obtained from direct digestion of total (or pre-fractioned) proteins. In particular, peptide mixtures are first separated by means of ion-exchange chromatography (SCX column, 5 µm, 0.3 ID×150 mm) using seven steps of increasing ammonium chloride concentration (0 to 1000 mM). Each salt step is directly loaded onto the reversed phase column ($C_{18}$, 0.180 ID×100 mm) and separated with an acetonitrile gradient: eluent A, 0.1% formic acid in water; eluent B, 0.1% formic acid in acetonitrile. Peptides eluted from the $C_{18}$ column are analyzed directly with an ion trap mass spectrometer; the limit of detection is around 10 fmol or less. Spectra are acquired in positive mode (typically in the range of 400-1600 m/z) using dynamic exclusion for MS/MS analysis. Different proteases are used to digest the protein extract from samples (trypsin, pepsin or proteinase K).

The identification of the corresponding proteins is then obtained through an automated database search with appropriate software, such as the SEQUEST algorithm (Eng, J. K., McKormack, A. L., Yates, J. R. "An Approach to Correlate Tandem Mass Spectra Data of Peptides with Amino Aminoacid Sequences in a Protein Database" J. Am. Soc. Mass Spectrom., 1994, 5, 976-984) for data handling of mass spectra. The experimental mass spectra produced are correlated to peptide sequences obtained by comparison with the theoretical mass spectra in the protein database downloaded from the NCBI (.ncbi.nlm.nih.gov) or other websites.

1.5 Criteria for Protein Identification

Peptide identifications were accepted if they could be established at greater than 90.0% probability as specified by the Peptide Prophet algorithm (Keller A., Nesvizhskii A. I., Kolker E., Aebersold R. "Empirical statistical model to estimate the accuracy of peptide identifications made by MS/MS and database search" Anal. Chem., 2002, 15, 5383-92). Protein identifications were accepted if they could be established at greater than 95.0% probability and contained at least one identified peptide. Because not more than 50% identity was found with the protein public databases, the genome of *Actinoallomurus* was sequenced and translated in the 6 possible reading frames. Subsequent alignement by BLAST of the detected peptides against the *Actinoallomurus* putative proteins identified the known homologue proteins.

A total of 94 proteins were putatively identified in the secretome of *Actinoallomurus*. Enzymes constituted a significant fraction of them, 17 proteolytic enzymes were detected, and glycosidases, lipases, acid phosphatases and diesterases were also found. No function could be assigned by BLAST analysis to 25 sequences.

Among the proteases, five proteins belonging to the S8/S53 peptidase family could be detected, two of which were among the most represented proteins.

The same analyses were performed onto all subsequent purification steps until only few sequences were detected.

The data obtained by the MS analysis of the boiled active fractions showed few protein sequences although a single band was present on silver stained SDS-PAGE gel. As shown in Table 1, endopep-140 (SEQ ID NO: 1) and endopep-40 (SEQ ID NO: 2) were detected as the proteins responsible of the two described activities. The presence of endopep-140 in the sample identified as <100 kDa is possibly due to partial degradation of the protein in smaller polypeptides.

The in silico analysis indicated that both endopep-140 and endopep-40 are glycosylated proteins containing a signal peptide leading to secretion suggesting that they may be produced as preproenzymes.

The in silico analysis grouped all the five endopeps in the S8/S53 family and indicated that all are glycosylated proteins. High homology was found among endopep-140, endopep-40 and endopep-41 (SEQ ID NO: 5) allowing their clustering in a subgroup as shown by the phylogenetic tree of FIG. 1. A signal peptide sequence was detected also for endopep-60 (SEQ ID NO: 4), while it was absent in endopep-120 (SEQ ID NO: 3) and endopep-41. The phylogenetic tree shown in FIG. 1 highlighted the novelty of these S8/S53 glutenases, which do not cluster with kumamolisin nor sedolisin nor with the tripeptidyl-peptidase enzymes (sedA to sedD) disclosed in WO 2011/077359, that belong to the S53 family.

The novelty of these enzymes were further supported by substrate specificity, as shown in Example 3. The degradation pattern of 33-mer obtained by digestion with the endopep-140 or endopep-40 showed an endo-proteolytic activity.

Example 2: Endopeptidase Production in Recombinant Host Cells 2.1 Strains and Plasmids

*Actinoallomurus* sp. DSM 24988 was used in this study. All plasmid subcloning experiments were performed in *E. coli* DH10B (Invitrogen, Carlsbad, Calif.) using the plasmid pTZ57R/T (Fermentas, UAB, Lithuania).

*Escherichia coli* BL21(DE3) Star(Novagen Italia, Podenzano, PC) was used to produce heterologous (recombinant) peptidases.

2.2 Recombinant Protease Production

Recombinant *Actinoallomurus* proteases were produced and purified from *Escherichia coli* BL21 (DE3) Star used as the expression system.

To construct *E. coli* strains producing Endopep-140 and Endopep-40 nucleotide sequences of genes were amplified using the following set of primers:

```
Fendopep-140
                                          SEQ ID NO: 12
5'-AAAAAGCTTCAGCTACAGGTGTGGTCGG-3'

Rendopep-140
                                          SEQ ID NO: 13
5'-AAAAAAACATATGCCCGATCTTCCCACCC-3'

Fendopep-40
                                          SEQ ID NO: 14
5'-AAAAAGCTTCAGAAGGCTCCGGTGCC-3'

Rendopep-40
                                          SEQ ID NO: 15
5'-AAAAAAACATATGTCACGACGCGTGACCG-3'
```

The PCR products were cloned into the pTZ57R/T vector and sequenced prior to cloning into the expression vector to verify that no mutation had been introduced during PCR amplifications.

Then endopep-genes were cloned into the NdeI-HindIII sites of pET28b plasmid (Novagen) and transformed into the expression host BL21(DE3) Star.

The transformed cells were grown in 50 ml cultures of LB media containing 30 µ/ml of kanamycin at 37° C. until OD600 0.6-1 was achieved. The expression of glutenases was induced with the addition of 0.2 µM isopropyl β-D-thiogalactoside (Sigma) and the cultures were further incubated at 22° C. overnight. As shown in FIG. 4, protein bands corresponding to the desired molecular weight of endopep-140 and endopep-40 were obtained.

2.3 Purification of Heterologously Produced Endopeptidase(s).

The cells expressing the recombinant endopeptidases were centrifuged at 5000 g for 20 minutes. The pellet was resuspended in 8 ml of buffer solution (20 mM sodium phosphate 500 mM NaCl, pH 7.8), then lysozyme 1 mg/ml was added to lyse the cells completely. His-tagged proteins were purified from crude cell extracts by immobilized $Ni^{2+}$-affinity chromatography using the Ni-NTA Purification System (Invitrogen) according to the manufacturer's instructions. Five microliters aliquots of eluted fractions were migrated through a SDS-PAGE and stained with blue-coomassie or silver staining to verify the presence and the degree of purity of the expressed endopeptidases. FIG. 4 shows the expression levels obtained for endopep-140 and endopep-40 after induction compared to the non-induced control strain.

Enzymatic activity of the total extracts obtained from *E. coli* strains transformed with pET28b empty and pET28b-endopep-140 or pET28b-endopep-40 respectively was tested with Succinyl-Ala-Ala-Pro-Phe-AMC as a substrate. Enzymatic activity was detected in the extracts from pET28b-endopeps strains while no activity was shown by the negative control.

Example 3: Endopeptidase Biological Activity 3.1 Degradation of 33-Mer Toxic Peptide of Gliadin at Acidic pH A solution of 33-mer immunotoxic peptide of gliadin (50 µM) was incubated at 37° C. for up to 2 hours in the presence of 4 µU of endopep-140 or 2 µU endopep-40 in presence or absence of pepsin 1 mg/ml. The reaction was carried out in acetic acid 20 mM pH 3, total volume of 300 µl. The reaction was monitored at different times from 0 to 120 min (t0, t3, t15, t30, t60 and t120 min) at 37° C. Disappearance of the 33-mer peptide and appearance of degradation products was monitored by HPLC-MS analysis. 50 µl aliquots were taken and the enzyme activity was stopped with 50 µl $H_2O$:$CH_3CN$ 50:50 (+0.1% formic acid). The samples were submitted to HPLC-MS, analyzed on LTQ-XL mass spectrometer (Thermo Fisher Scientific, San Jose, Calif., USA). The HPLC-MS profiles obtained with endopep-140, endopep-140 and pepsin, pepsin alone are reported in FIGS. 5, 6, 7 respectively. The disappearance of the 33-mer peptide was evident after 2 h incubation.

All peptides detected after incubation of the 33-mer peptide with 4 µU of endopep-140 or 2 µU of endopep-40 are reported in tables 2 and 3, respectively.

After 2 hours incubation, the most intense peak observed has a charge status of 1 and corresponds to $[MH]^+$ of 748.4, indicating the presence of small peptides. This signal is also the first to appear. On the basis of the 33-mer sequence, four (1-6, 8-13, 15-20, 22-27) peptides correspond to this molecular mass, all being composed of 6 residues. According to the MS analysis of the digested 33-mer, glutamic residues instead of glutamine residues are present in the hydrolyzed peptide sequence, thus suggesting a deamidation of the substrate.

The analysis showed that after 2 hours of incubation of 33-mer with pepsin almost no hydrolysis was observed (FIG. 7 and Tables 2 and 3) in agreement with literature data.

Increasing the amount of endopep-140 up to 8 µU or of endopep-40 to 9 µU resulted in complete 33-mer disappearance after 2 h at pH 3 (not shown).

Even in the presence of pepsin the same pattern of degradation is observed although the amount of intact peptide after 2 h is higher than in its absence, suggesting that the endopeptidases are not destroyed by pepsin.

3.2 HPLC/MS Analysis

HPLC analysis were performed using ion trap mass spectrometer. LTQ-XL or Advantage coupled to Accela or Surveyor pump (Thermofisher Scientific, San Jose, Calif., USA) were used in characterising the enzymatic protein hydrolyzates produced by the enzyme mixture. The peptides were separated using a Thermofisher Scientific Hypersil gold or a C18 symmetry column (Waters, Milford, Mass., USA) in combination with a gradient of 0.1% formic acid in Milli Q water (Millipore, Bedford, Mass., USA) (Solution A) and 0.1% formic acid in acetonitrile (Solution B) for elution. The gradient started at 95% of Solution A and increased to 60% of Solution B. Detailed information on the individual peptides was obtained by using the "scan dependent" MS/MS algorithm, which is a characteristic algorithm for an ion trap mass spectrometer. Full scan analysis was followed by zoom scan analysis for the determination of the charge state of the most intense ion in the full scan mass range. 33-mer (M=3910) was used to tune for optimal sensitivity in MS mode and for optimal fragmentation in MS/MS mode, performing constant infusion of 60 µg/ml, resulting in mainly doubly and triply charged species in MS mode, and an optimal collision energy of about 35% in MS/MS mode.

Example 4: Endopeptidase Biological Activity 4.1 Degradation of Gliadin and Gluten Hydrolyzed Mixture Owing to a specific structural feature, prolyl oligopeptidases cannot digest large peptides, usually longer than 30 aminoacids. Also, the tripeptidyl-protease sedolisin cannot hydrolyze gliadin without prolyl protease addition. This limitation is an obvious disadvantage for an enzyme, which is meant to hydrolyze as quickly and as efficiently as possible all potential toxic proline-rich peptides.

Endopep-140 and endopep-40 from *Actinoallomurus* were incubated with gliadins to see if the *Actinoallomurus* endoproteases are able to digest the whole proteins. The hydrolysis products formed were analyzed by SDS-PAGE.

A solution of gliadin was prepared by dissolving gliadin powder (Sigma G3375) in ethanol 70% at 70° C. at a concentration of 10 mg/ml (20 µM). The intact gliadin molecules consist of a protein mixture of 40-55 kDa. Gliadin was incubated at 37° C. with 10 µl (5 µU) of the *Actinollomurus* endoproteases in acetic acid 20 mM pH 3 in a final volume of 0.3 ml. The reactions were performed in a Thermomixer (Eppendorf AG, Hamburg, Germany) both in the absence and in the presence of pepsin at 1 mg/ml (FIG. 8). The reactions were monitored at different times interval, 30 µl samples were withdrawn from the incubation mixture at time 0 min, 30 min, 1 and 2 h and kept at 4° C. until SDS-PAGE. All materials used for SDS-PAGE and staining were purchased from Bio-Rad (Bio-Rad Laboratories, Inc., Hercules, Calif., USA). Samples were prepared using sample buffer according to manufactures instructions and separated on any kd Bis-Tris gels using SDS buffer system according to manufactures instructions. Staining was performed using Coomassie R250 or silver.

As it can be seen in FIG. 8, gliadin is cleaved by the *Actinollomurus* derived endopeptidases into small peptides to almost complete digestion in 2 hours. The decay of the product can be seen by the decrease in intensity of the band on the SDS gel. This experiment also shows that pepsin does not affect the efficacy of the digestion.

TABLE 1

Putative proteins purified from *Actinoallomurus* secretome. *Actinoallomurus* purified fractions were filtered on 100 kDa molecular weight cut-off and submitted to MS-shotgun analysis. Identified peptides were aligned against proteins inferred by *Actinoallomurus* genome translation (Protein_Id: internal code for putative protein sequence) and subsequent in silico analysis by BLAST evidenced the homologue known proteins (BLAST accession number: sequence code; BLAST annotation: protein name; n.r.: no result). Numbers of matched spectra give a semiquantitative measure of protein amounts, indicated as frequence (F_average).
A: data obtained from >100 kDa fraction;
B: data obtained from <100 kDa fraction

| Protein_Id | BLAST accession number | BLAST annotation | F_Average | notes |
|---|---|---|---|---|
| A |  |  |  |  |
| Seq_48773 | YP_003835151.1 | Peptidase S8/S53 | 101.9 | Endopep-140 |
| Seq_100531 | dbj\|BAJ32040.1 | putative lipase | 20.2 |  |
| Seq_293141 | n.r. | n.r. | 10.14 |  |
| B |  |  |  |  |
| Seq_44766 | ZP_06921971.1 | secreted protein | 40.14 |  |
| Seq_72108 | YP_003114375.1 | Peptidase S8/S53 | 30.25 | Endopep-40 |
| Seq_48773 | YP_003835151.1 | Peptidase S8/S53 | 20.15 | Endopep-140 |
| Seq_293141 | n.r. | n.r. | 10.15 |  |

TABLE 2

Peptides released by 33-mer digestion with endopep-140.
All molecular weights detected by HPLC-MS after digestion of 33-mer gliadin peptide (50 μM) with 4 μU endopep-140 in the presence and absence of pepsin (1 mg/ml). Control is obtained by incubating the 33-mer with pepsin alone. Incubation at 37° C., acetic acid 20 mM, pH 3.

```
 1           5              10             15             20             25             30
 L  Q  L  Q  P  F  P  Q  P  O  L  P  Y  P  Q  P  Q  L  P  Y  P  Q  P  Q  L  P  Y  P  Q  P  Q  P  F
```

| Incubation time | Mass signal | Charge status | Deduced peptide sequence | Notes |
|---|---|---|---|---|
| $T_0$ | 1306.27; 1956.64 | 3 $[M - 3H^{1+}]$; 2 $[M - 2H]^+$ | 1-33 | 100% residual |
| $T_{30}$ | 1088.73 | 1 $[MH]^+$ | 25-33 |  |
|  | 1197.45 | 1 $[MH]^+$ | 1-10 |  |
|  | 748.45 | 1 $[MH]^+$ | 1-6; 8-13; 15-20; 22-27 |  |
|  | 1306.27; 1956.64 | 3 $[M - 3H^{1+}]$; 2 $[M - 2H]^+$ | 1-33 | 50% residual |
| $T_{30}$ + pepsin | 1088.73 | 1 $[MH]^+$ | 25-33 |  |
|  | 1197.45 | 1 $[MH]^+$ | 1-10 |  |
|  | 748.45 | 1 $[MH]^+$ | 1-6; 8-13; 15-20; 22-27 |  |
|  | 1306.27; 1956.64 | 3 $[M - 3H^{1+}]$; 2 $[M - 2H]^+$ | 1-33 | 70% residual |
| $T_{2h}$ | 1088.73 | 1 $[MH]^+$ | 25-33 |  |
|  | 1197.45 | 1 $[MH]^+$ | 1-10 |  |
|  | 748.45 | 1 $[MH]^+$ | 1-6; 8-13; 15-20; 22-27 | Most intense peak |
|  | 1068.24 | 1 $[MH]^+$ | 16-24 |  |
|  | 845.27 | 1 $[MH]^+$ | 1-7 | traces |
|  | 1306.27; 1956.64 | 3 $[M - 3H^{1+}]$; 2 $[M - 2H]^+$ | 1-33 | 20% residual |
| $T_{2h}$ + pepsin | 1088.8 | 1 $[MH]^+$ | 25-33 |  |
|  | 1197.45 | 1 $[MH]^+$ | 1-10 |  |
|  | 748.45 | 1 $[MH]^+$ | 1-6; 8-13; 15-20; 22-27 |  |
|  | 1068.24 | 1 $[MH]^+$ | 16-24 |  |
|  | 845.27 | 1 $[MH]^+$ | 1-7 |  |
|  | 1306.27; 1956.64 | 3 $[M - 3H^{1+}]$; 2 $[M - 2H]^+$ | 1-33 | 45% residual |
| Control $T_{2h}$ | 1306.27; 1956.64 | 3 $[M - 3H^{1+}]$; 2 $[M - 2H]^+$ | 1-33 | 95% residual |

TABLE 3

Peptides released by 33-mer digestion with endopep-40.
All molecular weights detected by HPLC-MS after digestion of 33-mer gliadin peptide (50 μM)
with 2 μU endopep-40 in the presence and absence of pepsin (1 mg/ml) at different
time intervals. Control is obtained by incubating the 33-mer with pepsin alone. Incubation
at 37° C., acetic acid 20 mM, pH 3.

SEQ ID NO: 6

```
1       5          10         15         20         25         30
L Q L Q P F P Q P O L P Y P Q P Q L P Y P Q P Q L P Y P Q P Q P F
```

| Incubation time | Mass signal | Charge status | Deduced peptide sequence | notes |
|---|---|---|---|---|
| T$_0$ | 1306.27; 1956.64 | 3 [M − 3H]$^{1+}$; 2 [M − 2H]$^{+}$ | 1-33 | 100% residual |
| T$_{30}$ | 1197.45 | 1 [MH]$^{+}$ | 1-10 | |
|  | 1088.73 | 1 [MH]$^{+}$ | 25-33 | |
|  | 748.45 | 1 [MH]$^{+}$ | 1-6; 8-13; 15-20; 22-27 | |
|  | 1306.27; 1956.64 | 3 [M − 3H]$^{1+}$; 2 [M − 2H]$^{+}$ | 1-33 | 50% residual |
| T$_{30}$ + pepsin | 1088.73 | 1 [MH]$^{+}$ | 25-33 | |
|  | 1197.45 | 1 [MH]$^{+}$ | 1-10 | |
|  | 748.45 | 1 [MH]$^{+}$ | 1-6; 8-13; 15-20; 22-27 | |
|  | 1306.27; 1956.64 | 3 [M − 3H]$^{1+}$; 2 [M − 2H]$^{+}$ | 1-33 | 70% residual |
| T$_{2\,h}$ | 1088.73 | 1 [MH]$^{+}$ | 25-33 | |
|  | 1197.45 | 1 [MH]$^{+}$ | 1-10 | |
|  | 748.45 | 1 [MH]$^{+}$ | 1-6; 8-13; 15-20; 22-27 | |
|  | 1306.27; 1956.64 | 3 [M − 3H]$^{1+}$; 2 [M − 2H]$^{+}$ | 1-33 | 20% residual |
| T$_{2\,h}$ + pepsin | 1088.8 | 1 [MH]$^{+}$ | 25-33 | |
|  | 1197.45 | 1 [MH]$^{+}$ | 1-10 | |
|  | 748.45 | 1 [MH]$^{+}$ | 1-6; 8-13; 15-20; 22-27 | |
|  | 1306.27; 1956.64 | 3 [M − 3H]$^{1+}$; 2 [M − 2H]$^{+}$ | 1-33 | 30% residual |
| Control T$_{2\,h}$ | 1306.27; 1956.64 | 3 [M − 3H]$^{1+}$; 2 [M − 2H]$^{+}$ | 1-33 | 95% residual |

---

The invention claimed is:

1. A method for the treatment of a disorder associated with intolerance to the gliadin peptide of SEO ID NO. 6, which comprises administering to a patient in need thereof an effective amount of an enzyme composition comprising one or more polypeptides comprising an endopeptidase of the S8/S53 family selected from the group consisting of:
the endopep-40 set forth by SEQ ID NO: 2,
a fragment of the endopep-40 set forth by SEQ ID NO: 2, said fragment having endopeptidase activity at a pH between 3 and 8, and
an endopeptidase having at least 95% identity to SEQ ID NO: 2 and having endopeptidase activity at a pH between 3 and 8.

2. The method according to claim 1, wherein said endopeptidase is selected from the group consisting of:
the endopep-40 set forth by SEQ ID NO: 2, and
an endopeptidase having at least 95% of identity to SEQ ID NO: 2 and having endopeptidase activity at a pH between 3 and 8.

3. The method according to claim 1, wherein the endopeptidase is obtainable from an *Actinoallomurus* strain.

4. The method according to claim 3, wherein the endopeptidase is obtainable from the *Actinoallomurus* sp DSM24988.

5. The method according to claim 1, wherein said enzyme composition comprises one or more other proteolytic enzymes selected from prolyl-endoproteases, x-prolyldipeptidyl aminopeptidases, and prolyl-aminopeptidases.

6. The method according to claim 1 or 5, wherein the enzyme composition is incorporated into a food supplement.

7. The method according to claim 1, wherein said polypeptide comprises the endopep-40 set forth by SEQ ID NO: 2.

8. A method for the treatment of a disorder associated with intolerance to gliadin peptide of SEQ ID NO: 6, which comprises pretreating foodstuff, prior to ingestion by a patient in need thereof,
with an effective amount of an enzyme composition comprising one or more polypeptides comprising an endopeptidase of the S8/S53 family selected from the group consisting of:
the endopep-40 set forth by SEQ ID NO: 2,
a fragment of the endopep-40 set forth by SEQ ID NO: 2 having endopeptidase activity at a pH between 3 and 8, and
an endopeptidase having at least 95% of identity to SEQ ID NO: 2 and having endoprotease activity at a pH between 3 and 8.

9. The method according to claim 8, wherein said endopeptidase is selected from the group consisting of:
the endopep-40 set forth by SEQ ID NO: 2, and
an endopeptidase having at least 95% of identity to SEQ ID NO: 2 and having endopeptidase activity at a pH between 3 and 8.

10. The method according to claim 8, wherein said polypeptide comprises the endopep-40 set forth by SEQ ID NO: 2.

11. The method according to claim 8, wherein the endopeptidase is obtainable from an *Actinoallomurus* strain.

12. The method according to claim 11, wherein the endopeptidase is obtainable from the *Actinoallomurus* sp DSM24988.

* * * * *